(12) United States Patent
Ikami

(10) Patent No.: US 10,417,790 B2
(45) Date of Patent: Sep. 17, 2019

(54) SHADING CORRECTION APPARATUS AND METHOD FOR OPERATING SHADING CORRECTION APPARATUS

(71) Applicant: FUJIFILM Corporation, Tokyo (JP)

(72) Inventor: Seishi Ikami, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 197 days.

(21) Appl. No.: 15/684,153

(22) Filed: Aug. 23, 2017

(65) Prior Publication Data

US 2018/0061085 A1 Mar. 1, 2018

(30) Foreign Application Priority Data

Aug. 24, 2016 (JP) .................................. 2016-163728

(51) Int. Cl.
*G06T 11/00* (2006.01)
*G06T 5/50* (2006.01)
*H04N 1/407* (2006.01)
*G01N 27/447* (2006.01)
*G01N 21/64* (2006.01)

(52) U.S. Cl.
CPC ............. *G06T 11/001* (2013.01); *G06T 5/50* (2013.01); *H04N 1/4076* (2013.01); *G01N 21/6456* (2013.01); *G01N 27/44721* (2013.01); *G06T 2207/10064* (2013.01)

(58) Field of Classification Search
CPC .................... G06T 11/001; G06T 5/50; G06T 2207/10064; H04N 1/4076; G01N 21/6456; G01N 27/44721
See application file for complete search history.

(56) References Cited

U.S. PATENT DOCUMENTS

2005/0270639 A1* 12/2005 Miki .................. G02B 21/0088
359/381
2009/0294701 A1 12/2009 Ebisawa et al.
2018/0313760 A1* 11/2018 Kramer ............. G01N 21/6456

FOREIGN PATENT DOCUMENTS

JP     11-355568 A    12/1999
JP     2003-315944 A  11/2003

OTHER PUBLICATIONS

Extended European Search Report, dated Jan. 22, 2018, for corresponding European Application No. 17186699.9.

* cited by examiner

*Primary Examiner* — Phuoc Tran
(74) *Attorney, Agent, or Firm* — Birch, Stewart, Kolasch & Birch, LLP

(57) ABSTRACT

A first resin plate includes a phthalocyanine-based pigment as an organic fluorescent material and is used for shading correction in a case in which infrared excitation light with a center wavelength of 770 nm to 800 nm. A second resin plate includes an anthraquinone-based pigment as the organic fluorescent material and is used for shading correction in a case in which red excitation light with a center wavelength of 650 nm to 690 nm. An acquisition unit acquires a reference image obtained by irradiating the resin plates with the infrared excitation light and the red excitation light, respectively. A correction unit performs shading correction for a fluorescence image on the basis of the reference image.

19 Claims, 17 Drawing Sheets

| | FIRST RESIN PLATE (FIRST CORRECTION TOOL) | SECOND RESIN PLATE (SECOND CORRECTION TOOL) |
|---|---|---|
| ORGANIC FLUORESCENT MATERIAL | PHTHALOCYANINE-BASED PIGMENT | ANTHRAQUINONE-BASED PIGMENT |
| EXCITATION WAVELENGTH | 770nm TO 800nm | 625nm TO 645nm<br>650nm TO 690nm |
| EMISSION WAVELENGTH | 845nm | 720nm | ns # SHADING CORRECTION APPARATUS AND METHOD FOR OPERATING SHADING CORRECTION APPARATUS

CROSS-REFERENCE TO RELATED APPLICATION

This application claims priority under 35 USC 119 from Japanese Patent Application No. 2016-163728, filed 24 Aug. 2016, the disclosure of which is incorporated by reference herein.

BACKGROUND OF THE INVENTION

1. Field of the Invention

The present invention relates to a shading correction apparatus and a method for operating the shading correction apparatus.

2. Description of the Related Art

An image reading apparatus has been known which irradiates an image carrier that carries image information and includes a fluorescent material with excitation light, detects fluorescent light emitted from the fluorescent material excited by the excitation light, and outputs a fluorescence image. The image carrier includes a material obtained by fluorescently labeling a biological material, such as deoxyribonucleic acid (DNA), ribonucleic acid (RNA), or protein, as a sample with a fluorescent pigment or fluorescent protein that has fluorescent properties caused by gene expression.

There are a plurality of kinds of fluorescent materials including fluorescent pigments or fluorescent protein. The fluorescent materials have different excitation wavelengths and emission wavelengths. Therefore, as excitation light sources that emit excitation light, excitation light sources having different emission wavelength bands of excitation light are prepared. Specifically, for example, the following excitation light sources are used: an infrared excitation light source that emits infrared excitation light with a center wavelength of 770 nm to 800 nm; a red excitation light source that emits red excitation light with a center wavelength of 625 nm to 645 nm or a center wavelength of 650 nm to 690 nm; a green excitation light source that emits green excitation light with a center wavelength of 520 nm to 540 nm; and a blue excitation light source that emits blue excitation light with a center wavelength of 460 nm to 490 nm. The center wavelength is the wavelength of the center of the width (half width) of half the maximum intensity of the emission spectrum of excitation light of each color.

In the image reading apparatus, in some cases, shading which is density unevenness caused by the configuration of the apparatus occurs in a fluorescence image. A technique has been proposed which uses a correction tool in order to correct the shading. The correction tool includes a fluorescent material having wavelength characteristics in which an excitation wavelength band and an emission wavelength band at least partially overlap an excitation wavelength band and an emission wavelength band of the fluorescent material in the image carrier, respectively.

For example, JP1999-355568A (JP-H11-355568A) discloses a correction tool including an inorganic fluorescent material such as a cerium-activated yttrium aluminum garnet (YAG) phosphor (YAG:Ce). In JP1999-355568A (JP-H11-355568A), the correction tool including the inorganic fluorescent material corrects shading in a case in which green excitation light with a center wavelength of 530 nm to 540 nm and blue excitation light with a center wavelength of 470 nm to 480 nm are used.

JP2003-315944A discloses a correction tool including an organic fluorescent material such as a vinyl chloride resin or a methacrylic resin. In JP2003-315944A, the correction tool including the organic fluorescent material corrects shading in a case in which red excitation light with a center wavelength of 640 nm, green excitation light with a center wavelength of 532 nm, and blue excitation light with a center wavelength of 473 nm are used.

JP1999-355568A (JP-H11-355568A) and JP2003-315944A do not disclose shading correction in a case in which infrared excitation light with a center wavelength of 770 nm to 800 nm and red excitation light with a center wavelength of 650 nm to 690 nm are used.

The organic fluorescent material disclosed in JP2003-315944A emits little fluorescent light or a very small amount of fluorescent light when it is excited by infrared excitation light with a center wavelength of 770 nm to 800 nm and red excitation light with a center wavelength of 650 nm to 690 nm. Therefore, the organic fluorescent material is not suitable for a correction tool for infrared excitation light with a center wavelength of 770 nm to 800 nm and red excitation light with a center wavelength of 650 nm to 690 nm.

A correction tool including the inorganic fluorescent material disclosed in JP1999-355568A (JP-H11-355568A) has been examined as the correction tool for infrared excitation light with a center wavelength of 770 nm to 800 nm and red excitation light with a center wavelength of 650 nm to 690 nm. However, since shading correction is correcting density unevenness in the entire fluorescence image, the correction tool requires the characteristic that it emits uniform fluorescent light from the entire surface in order to accurately perform shading correction. However, in a case in which the correction tool for infrared excitation light with a center wavelength of 770 nm to 800 nm and red excitation light with a center wavelength of 650 nm to 690 nm is formed by the inorganic fluorescent material disclosed in JP1999-355568A (JP-H11-355568A), it is difficult to achieve the required characteristic that uniform fluorescent light is emitted from the entire surface with high reproducibility.

As disclosed in paragraph [0015] of JP1999-355568A (JP-H11-355568A), a technique is also considered which manufactures a correction tool with a fluorescent pigment (for example, Cy3 (registered trademark)) that is used to fluorescently label a biological material. However, in this case, the fluorescent pigment used to fluorescently label a biological material is very expensive. In addition, since a large amount of discoloration occurs due to excitation, problems occur when the correction tool is used for a long time or is repeatedly used.

SUMMARY OF THE INVENTION

An object of the invention is to provide a shading correction apparatus that can accurately perform shading correction, particularly, shading correction in a case in which excitation light with a center wavelength greater than 650 nm is used, and a method for operating the shading correction apparatus.

In order to solve the above-mentioned problems, according to an aspect of the invention, there is provided a shading correction apparatus that is used in an image reading apparatus which irradiates an image carrier that carries image information and includes a fluorescent material with excitation light, detects fluorescent light emitted from the fluorescent material excited by the excitation light, and outputs a fluorescence image and corrects shading which is density unevenness in the fluorescence image. The shading correction apparatus comprises: a correction tool that includes an organic fluorescent material having wavelength characteristics in which an excitation wavelength band and an emission wavelength band at least partially overlap an excitation wavelength band and an emission wavelength band of the fluorescent material, respectively, and includes a first correction tool which includes a phthalocyanine-based pigment as the organic fluorescent material and/or a second correction tool which includes an anthraquinone-based pigment as the organic fluorescent material; and a processing circuitry configured to: acquire a reference image which is obtained by irradiating the correction tool with the excitation light and is a reference for the shading correction; and perform the shading correction for the fluorescence image on the basis of the reference image.

Preferably, the correction tool is used for the shading correction in a case in which the excitation light with a center wavelength greater than 650 nm is used. Preferably, the first correction tool is used for infrared excitation light with a center wavelength of 770 nm to 800 nm and the second correction tool is used for red excitation light with a center wavelength of 650 nm to 690 nm.

Preferably, the correction tool is a plate obtained by dispersing the organic fluorescent material in a binder and solidifying the binder.

Preferably, in a case in which the correction tool includes the first correction tool and the second correction tool, the first correction tool and the second correction tool are integrated with each other. In this case, preferably, a black plate is interposed between the first correction tool and the second correction tool. Alternatively, preferably, the first correction tool and the second correction tool are directly bonded to each other.

Preferably, the image reading apparatus includes a stage that holds the image carrier and an optical head that emits the excitation light, acquires the fluorescent light, and is moved relative to the stage. Preferably, the correction tool has a size that covers an entire scanning region of the optical head and is held by the stage.

Preferably, the image reading apparatus includes a stage that holds the image carrier and an optical head that emits the excitation light, acquires the fluorescent light, and is moved relative to the stage. Preferably, the correction tool is a cap type that is detachable from the optical head.

Preferably, a roughening process is performed for a surface of the correction tool. In this case, preferably, the roughening process is performed using any one of a solvent, fine particle powder, and a pressure die.

Preferably, the binder is any one of a vinyl chloride resin, a polycarbonate resin, a methacrylic resin, a silicone resin, and a polyacrylamide resin.

Preferably, the image reading apparatus includes a stage that holds the image carrier. Preferably, a liquid obtained by mixing the organic fluorescent material with a solvent is poured in the stage and the correction tool is formed by the stage and the liquid. Preferably, the solvent is mixed with a light diffusing material in addition to the organic fluorescent material. Preferably, the solvent is any one of ethanol, glycerin, and ethylene glycol, a mixed solution of at least two of ethanol, glycerin, and ethylene glycol, or an aqueous solution of any one of ethanol, glycerin, and ethylene glycol.

Preferably, the image reading apparatus includes a stage that holds the image carrier. Preferably, gel obtained by mixing the organic fluorescent material with a dispersion medium is poured in the stage and the correction tool is formed by the stage and the gel. Preferably, the dispersion medium is mixed with a light diffusing material in addition to the organic fluorescent material. Preferably, the dispersion medium is any one of agar, agarose, and polyacrylamide.

According to another aspect of the invention, there is provided a method for operating a shading correction apparatus that is used in an image reading apparatus which irradiates an image carrier that carries image information and includes a fluorescent material with excitation light, detects fluorescent light emitted from the fluorescent material excited by the excitation light, and outputs a fluorescence image and corrects shading which is density unevenness in the fluorescence image. The method comprises: acquiring a reference image which is a reference for the shading correction and is obtained by irradiating, with the excitation light, a correction tool that includes an organic fluorescent material having wavelength characteristics in which an excitation wavelength band and an emission wavelength band at least partially overlap an excitation wavelength band and an emission wavelength band of the fluorescent material, respectively, and includes a first correction tool which includes a phthalocyanine-based pigment as the organic fluorescent material and/or a second correction tool which includes an anthraquinone-based pigment as the organic fluorescent material; and performing the shading correction for the fluorescence image on the basis of the reference image.

According to still another aspect of the invention, there is provided a program for operating a shading correction apparatus that is used in an image reading apparatus which irradiates an image carrier that carries image information and includes a fluorescent material with excitation light, detects fluorescent light emitted from the fluorescent material excited by the excitation light, and outputs a fluorescence image and corrects shading which is density unevenness in the fluorescence image. The program causes a computer to perform: acquiring a reference image which is a reference for the shading correction and is obtained by irradiating, with the excitation light, a correction tool that includes an organic fluorescent material having wavelength characteristics in which an excitation wavelength band and an emission wavelength band at least partially overlap an excitation wavelength band and an emission wavelength band of the fluorescent material, respectively, and includes a first correction tool which includes a phthalocyanine-based pigment as the organic fluorescent material and/or a second correction tool which includes an anthraquinone-based pigment as the organic fluorescent material; and performing the shading correction for the fluorescence image on the basis of the reference image.

According to the invention, the correction tool including the first correction tool that includes a phthalocyanine-based pigment as the organic fluorescent material and/or the second correction tool that includes an anthraquinone-based pigment as the organic fluorescent material is used. Therefore, it is possible to provide a shading correction apparatus that can accurately perform shading correction, particularly, shading correction in a case in which excitation light with a center wavelength greater than 650 nm is used, and a method for operating the shading correction apparatus.

DESCRIPTION OF THE PREFERRED EMBODIMENTS

First Embodiment

Figure 1:
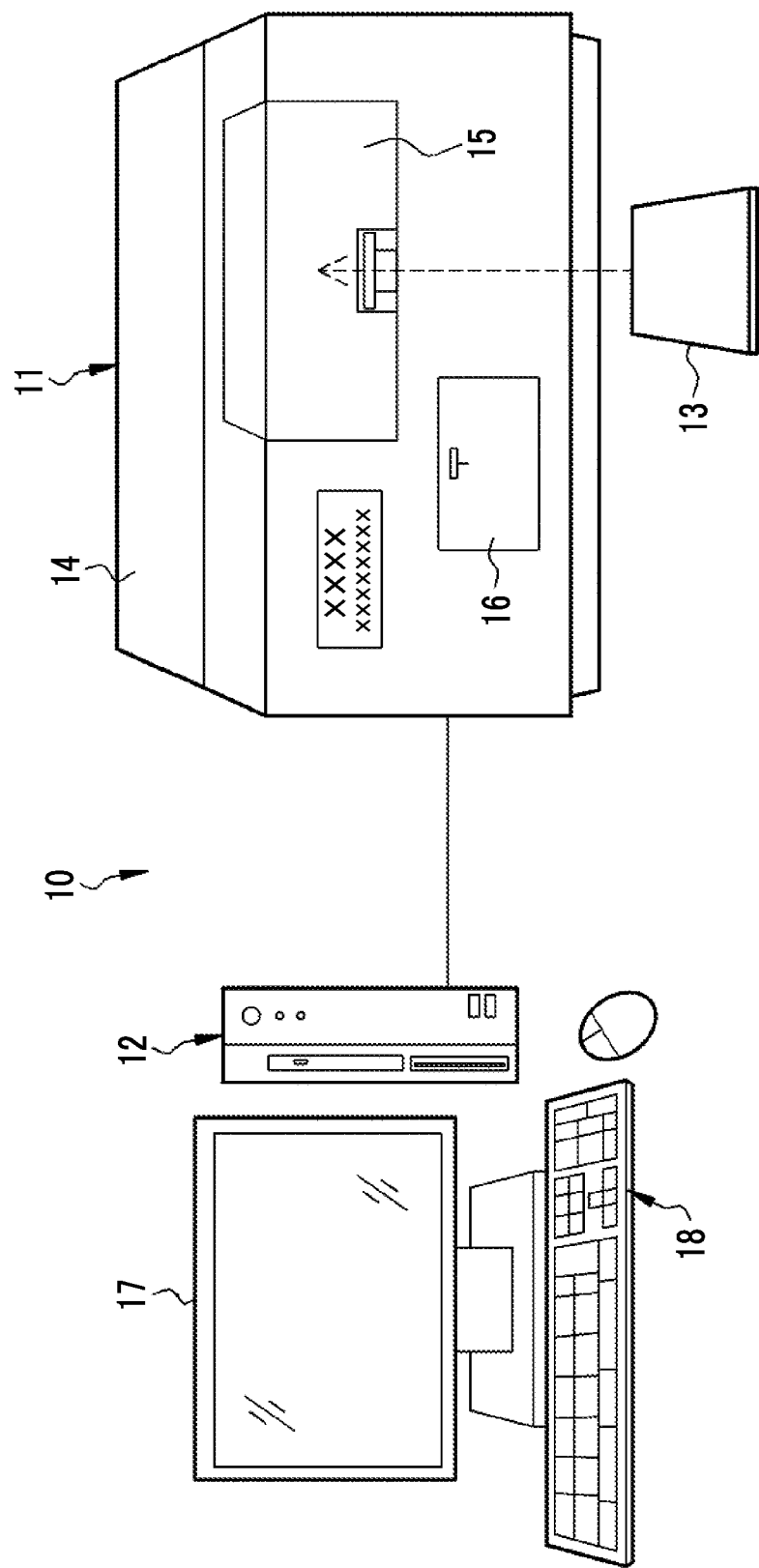
FIG. 1 is a diagram illustrating an image detection system.

In FIG. 1, an image detection system 10 comprises an image reading apparatus 11 and a console 12 corresponding to a shading correction apparatus. The image reading apparatus 11 and the console 12 are connected to each other by, for example, a universal serial bus (USB) communication cable such that they can exchange data.

The image reading apparatus 11 detects fluorescent light FL (see FIG. 2) from an image carrier 13 carrying image information and outputs a fluorescence image based on the detected fluorescent light FL. The image carrier 13 is a gel support or a transfer support on which an electrophoresis pattern of a biological material, such as DNA, RNA, or protein, as a sample or a biological material including fluorescent protein that has fluorescent properties caused by gene expression is recorded or a cell or a living tissue including the fluorescent protein.

The biological material is fluorescently labeled by a fluorescent pigment. In addition, the fluorescent protein has fluorescent properties. Therefore, the fluorescent light FL to be detected is emitted from a fluorescent material such as a fluorescent pigment or fluorescent protein. There are a plurality of kinds of fluorescent materials which have different excitation wavelengths and emission wavelengths.

For example, a fluorescent pigment C2 is excited by blue excitation light which will be described below and emits blue fluorescent light with a longer wavelength than the blue excitation light. A fluorescent pigment C3 is excited by green excitation light which will be described below and emits green fluorescent light with a longer wavelength than the green excitation light. A fluorescent pigment C5 is excited by red excitation light which will be described below and emits red fluorescent light with a longer wavelength than the red excitation light. The fluorescent pigment C2 is, for example, Cy2 (registered trademark). The fluorescent pigment C3 is, for example, Cy3 (registered trademark). The fluorescent pigment C5 is, for example, Cy5 (registered trademark). For example, in the case of green fluorescent protein (GFP), the fluorescent protein is excited by blue excitation light and emits green fluorescent light. In addition, for example, the following fluorescent protein has been known: yellow fluorescent protein (YFP) that is excited by green excitation light and emits yellow-green fluorescent light; and red fluorescent protein (RFP) that is excited by orange excitation light and emits red fluorescent light.

The entire image reading apparatus 11 is covered by a housing 14. The housing 14 shields the inside of the image reading apparatus 11 from external light that becomes noise in the detection of the fluorescent light FL. An openable and closable cover 15 for setting the image carrier 13 in the image reading apparatus 11 is provided on the front surface of the housing 14. In addition, reference numeral 16 indicates an openable and closable cover for replacing a filter unit 30 (see FIG. 2).

The console 12 is, for example, a desktop personal computer and includes a display 17 and an operation unit 18 including a keyboard and a mouse. The display 17 displays a screen that is used to operate the operation unit 18. The screen used for an operation forms a graphical user interface (GUI). The console 12 receives an operation command that is input from the operation unit 18 through the screen of the display 17.

Figure 2:
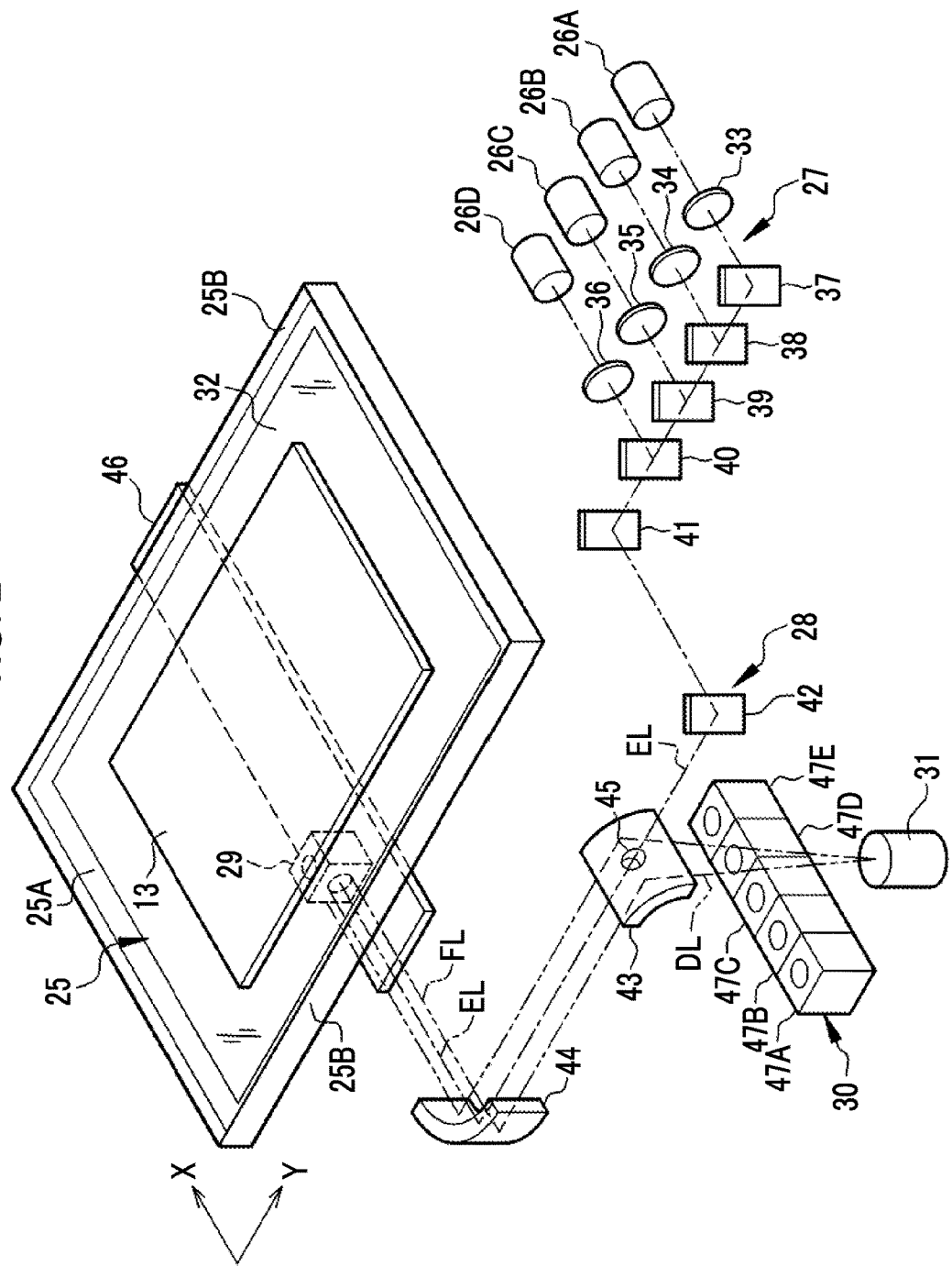
FIG. 2 is a diagram schematically illustrating an image reading apparatus.

In FIG. 2, the image reading apparatus 11 is provided with a stage 25, excitation light sources 26A, 26B, 26C, and 26D, a light source optical system 27, a light guide optical system 28, an optical head 29, a filter unit 30, and a photomultiplier 31.

The stage 25 holds the image carrier 13. The stage 25 has a bottom 25A that has a box shape surrounded by four side surfaces 25B. Most of the bottom 25A is hollowed and a transparent glass plate 32 is fitted to the hollowed portion. Therefore, in the glass plate 32, the area (hereinafter, referred to as a plane size) of the XY plane formed by a main scanning direction X and a sub-scanning direction Y is slightly less than the area of the bottom 25A. The glass plate 32 delimits a scanning region of the optical head 29. The image carrier 13 is placed on the glass plate 32.

The excitation light sources 26A to 26D emit the excitation light EL (represented by a one-dot chain line) of a fluorescent material. The excitation light sources 26A to 26D having different emission wavelength bands of the excitation light EL are prepared in order to respond to a plurality of kinds of fluorescent materials.

Specifically, the excitation light source 26A emits infrared excitation light with a center wavelength of 770 nm to 800 nm, for example, a center wavelength of 785 mm. The excitation light source 26B emits red excitation light with a center wavelength of 650 nm to 690 nm, for example, a center wavelength of 685 nm. The infrared excitation light and the red excitation light correspond to excitation light with a center wavelength greater than 650 nm. The center wavelength greater than 650 nm does not mean that the entire emission spectrum of excitation light is greater than 650 nm, but literally means that a point with a center wavelength, which is defined as the wavelength of the center of the width (half width) of half the maximum intensity of the emission spectrum of excitation light, is greater than 650 nm.

The excitation light source 26C emits green excitation light with a center wavelength of 520 nm to 540 nm, for example, a center wavelength of 532 nm. The excitation light source 26D emits blue excitation light with a center wavelength of 460 nm to 490 nm, for example, a center wavelength of 473 nm. The excitation light sources 26A, 26B, and 26D are, for example, semiconductor lasers and the excitation light source 26C is, for example, a second harmonic generation element.

Hereinafter, in some cases, the excitation light source 26A is referred to as an infrared excitation light source 26A, the excitation light source 26B is referred to as a red excitation light source 26B, the excitation light source 26C is referred to as a green excitation light source 26C, and the excitation light source 26D is referred to as a blue excitation light source 26D. In addition, in some cases, the excitation light sources 26A to 26D are collectively referred to as excitation light sources 26.

The emission wavelength band of the excitation light EL is not limited to the above. For example, the red excitation light source 26B may emit red excitation light with a center wavelength of 653 nm or a center wavelength of 655 nm, in addition to or instead of emitting the red excitation light with a center wavelength of 685 nm. In addition, the red excitation light source 26B may emit red excitation light with a center wavelength of 625 nm to 645 nm, for example, a center wavelength of 635 nm, in addition to emitting the red excitation light with a center wavelength of 650 nm to 690 nm. The blue excitation light source 26D may emit blue excitation light with a center wavelength of 488 nm, in addition to or instead of emitting the blue excitation light with a center wavelength of 473 nm. As such, the number of excitation light sources is not limited to 4 and may be 2 or 5 or more.

The light source optical system 27 includes collimator lenses 33, 34, 35, and 36, mirrors 37 and 41, and dichroic mirrors 38, 39, and 40. The collimator lenses 33 to 36 are provided on the front surfaces of the excitation light sources 26A to 26D, respectively, and collimate the excitation light components of each color emitted from the excitation light sources 26A to 26D. The mirror 37 reflects the infrared excitation light collimated by the collimator lens 33 to the dichroic mirror 38.

The dichroic mirror 38 transmits the infrared excitation light from the mirror 37 and reflects the red excitation light collimated by the collimator lens 34 to the dichroic mirror 39. The dichroic mirror 39 transmits the infrared excitation light from the mirror 37 and the red excitation light from the dichroic mirror 38 and reflects the green excitation light collimated by the collimator lens 35 to the dichroic mirror 40. The dichroic mirror 40 transmits the infrared excitation light from the mirror 37, the red excitation light from the dichroic mirror 38, and the green excitation light from the dichroic mirror 39 and reflects the blue excitation light collimated by the collimator lens 36 to the mirror 41.

The mirror 41 reflects the infrared excitation light which has been reflected by the mirror 37 and then transmitted through the dichroic mirrors 38 to 40, the red excitation light which has been reflected by the dichroic mirror 38 and then transmitted through the dichroic mirrors 39 and 40, the green excitation light which has been reflected by the dichroic mirror 39 and then transmitted through the dichroic mirror 40, and the blue excitation light which has been reflected by the dichroic mirror 40 to the light guide optical system 28.

The light guide optical system 28 includes a mirror 42, a perforated concave mirror 43, and a concave mirror 44. The mirror 42 reflects the excitation light EL from the mirror 41 of the light source optical system 27 to the perforated concave mirror 43. The perforated concave mirror 43 has a through hole 45 provided at the center. The excitation light EL from the mirror 42 is transmitted through the through hole 45 and travels toward the concave mirror 44. The concave mirror 44 reflects the excitation light EL transmitted through the through hole 45 to the optical head 29.

In addition, the fluorescent light FL (represented by a two-dot chain line) emitted from the optical head 29 is incident on the concave mirror 44. The concave mirror 44 reflects the fluorescent light FL to the perforated concave mirror 43. The perforated concave mirror 43 reflects the fluorescent light FL from the concave mirror 44 to the filter unit 30. As such, the perforated concave mirror 43 transmits the excitation light EL through the through hole 45 and reflects the fluorescent light FL to the filter unit 30 to branch the optical path of the excitation light EL and the fluorescent light FL.

The optical head 29 emits the excitation light EL to the image carrier 13 and acquires the fluorescent light FL from the image carrier 13. The optical head 29 is disposed on a substrate 46 which is an elongated plate and is provided below the stage 25. The optical head 29 can be moved on the substrate 46 in the main scanning direction X by, for example, a motor (not illustrated) or a rail (not illustrated). In addition, the substrate 46 and the concave mirror 44 can be moved in the sub-scanning direction Y by, for example, a motor (not illustrated) or a rail (not illustrated). That is, the optical head 29 can be moved in the main scanning direction X and the sub-scanning direction Y to scan the entire surface of the image carrier 13 with the excitation light EL and to acquire the fluorescent light FL from the entire surface of the image carrier 13. In addition, the optical head 29 may be fixed and the stage 25 may be moved in the main scanning direction X and the sub-scanning direction Y. That is, the optical head 29 may be configured so as to be moved relative to the stage 25.

The filter unit 30 is located on the optical path of the fluorescent light FL between the perforated concave mirror 43 and the photomultiplier 31. The filter unit 30 includes five filters 47A, 47B, 47C, 47D, and 47E which are arranged in the sub-scanning direction Y.

The filter unit 30 can be moved in the sub-scanning direction Y by, for example, a motor (not illustrated) or a rail (not illustrated), similarly to the substrate 46 and the concave mirror 44. Therefore, any one of the filters 47A to 47E is selectively disposed between the perforated concave mirror 43 and the photomultiplier 31. Specifically, in a case in which the image carrier 13 is a gel support or a transfer support, any one of the filters 47A to 47D is disposed between the perforated concave mirror 43 and the photomultiplier 31. In a case in which the image carrier 13 is a stimulable phosphor sheet, the filter 47E is disposed between the perforated concave mirror 43 and the photomultiplier 31.

The fluorescent light FL of the image carrier 13 includes a little amount of excitation light EL. The excitation light EL is noise that is unnecessary to generate a fluorescence image. Therefore, the filters 47A to 47E have the characteristic that they cut the excitation light EL and transmit the fluorescent light FL.

The filters 47A to 47D having different transmission wavelength bands are prepared in order to respond to a plurality of kinds of fluorescent materials, similarly to the excitation light sources 26A to 26D. Specifically, the filter 47A cuts light with a wavelength equal to or less than 785 nm (infrared excitation light) and transmits light with a wavelength greater than 785 nm (infrared fluorescent light). The filter 47B cuts light with a wavelength equal to or less than 685 nm (red excitation light) and transmits light with a wavelength greater than 685 nm (red fluorescent light). The filter 47C cuts light with a wavelength equal to or less than 532 nm (green excitation light) and transmits light with a wavelength greater than 532 nm (green fluorescent light). The filter 47D cuts light with a wavelength equal to or less than 473 nm (blue excitation light) and transmits light with a wavelength greater than 473 nm (blue fluorescent light).

Hereinafter, in some cases, the filter 47A is referred to as an infrared filter 47A, the filter 47B is referred to as a red filter 47B, the filter 47C is referred to as a green filter 47C, and the filter 47D is referred to as a blue filter 47D. Furthermore, in some cases, the filters 47A to 47E are collectively referred to as filters 47. Similarly to the emission wavelength band of the excitation light EL, the transmission wavelength band of the filter is not limited to the above. The number of filters is not limited to 5 and may be 2 or 6 or more.

The fluorescent light FL transmitted through the filters 47A to 47E is incident on the photomultiplier 31. The photomultiplier 31 photoelectrically detects the fluorescent light FL at a predetermined time and outputs an analog image signal corresponding to the detected fluorescent light FL.

Figure 3:
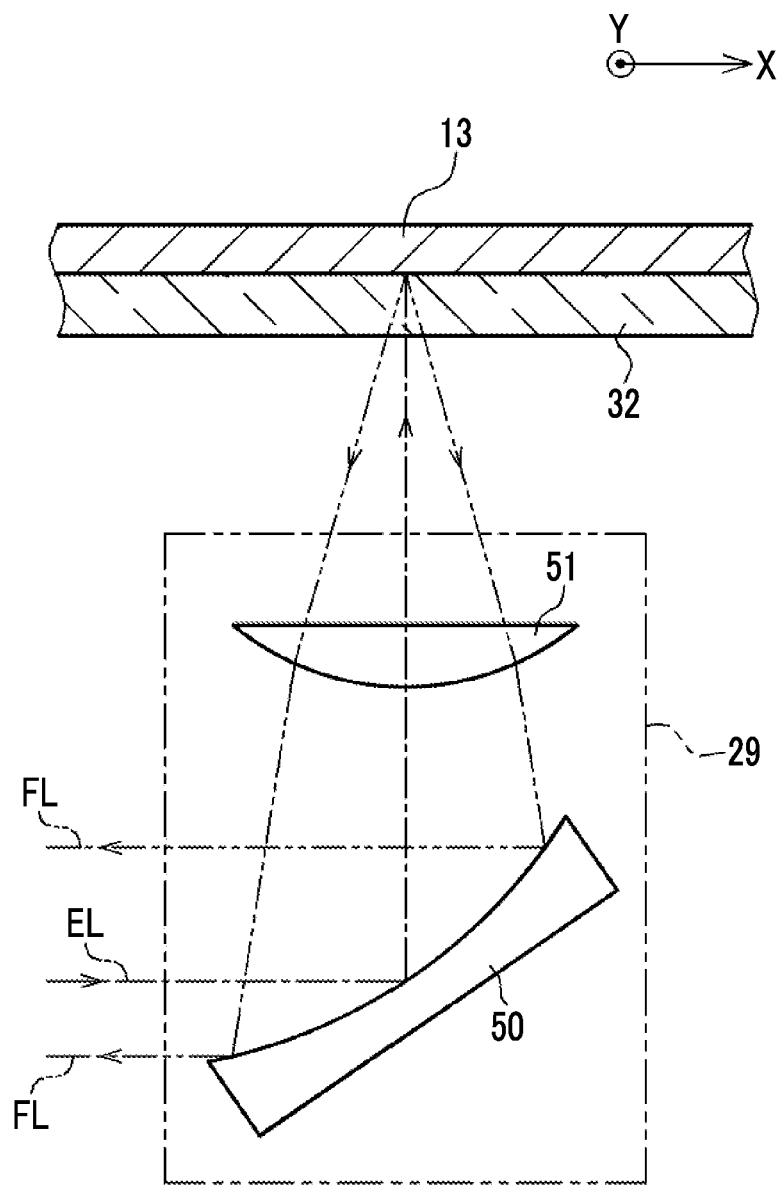
FIG. 3 is a diagram schematically illustrating an optical head.

As illustrated in FIG. 3, the optical head 29 is provided with a concave mirror 50 and an aspheric lens 51. The concave mirror 50 reflects the excitation light EL incident from the concave mirror 44 of the light guide optical system 28 to the aspheric lens 51. The aspheric lens 51 condenses the excitation light EL from the concave mirror 50 on a surface (a surface coming into contact with the glass plate 32) of the image carrier 13 placed on the glass plate 32. In addition, the aspheric lens 51 condenses the fluorescent light FL which is emitted from the image carrier irradiated with the excitation light EL such that the fluorescent light FL is incident on the concave mirror 50. The concave mirror 50 further condenses the fluorescent light FL from the aspheric lens 51 such that the fluorescent light FL is incident as substantially parallel light on the concave mirror 44 of the light guide optical system 28.

Figure 4:
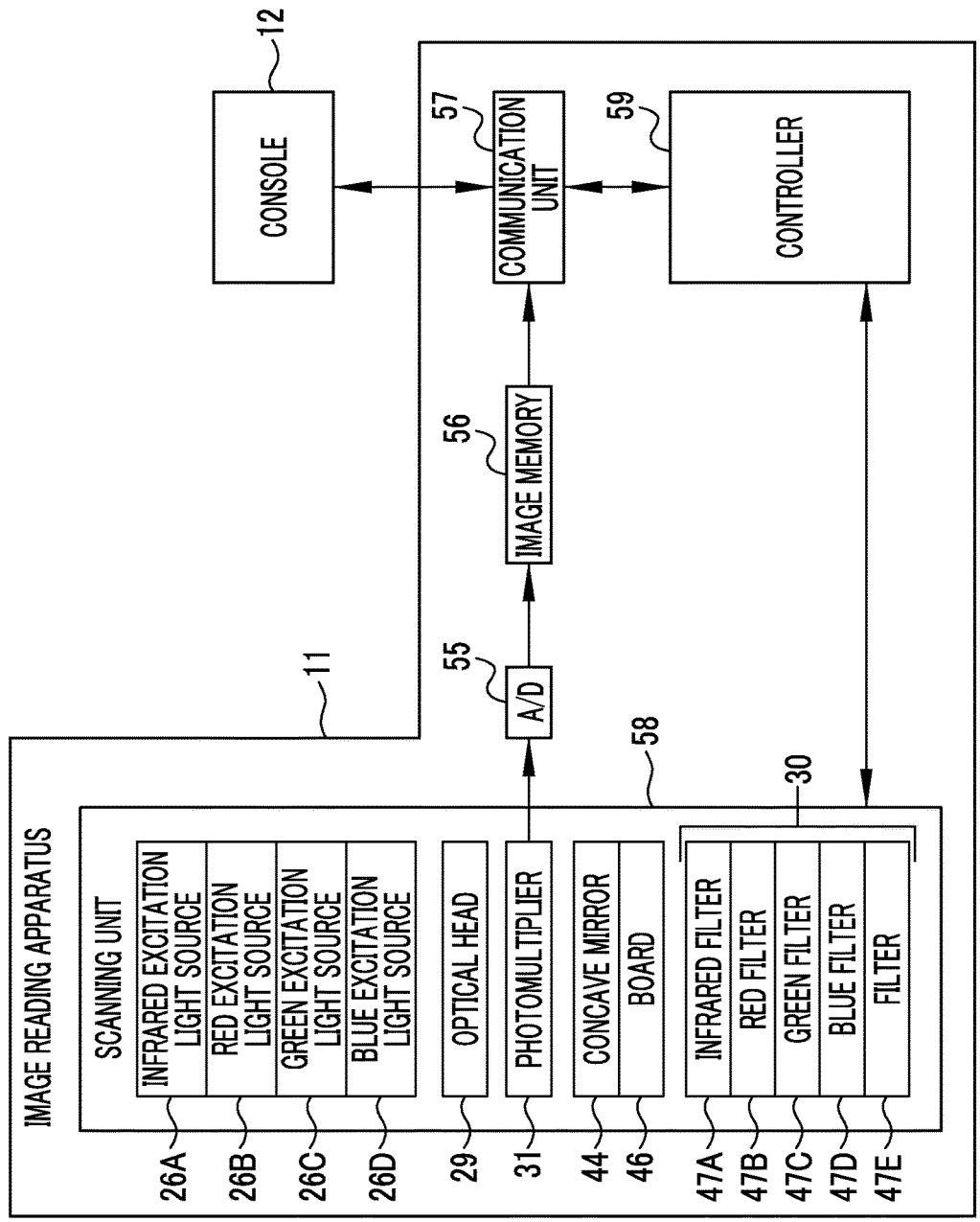
FIG. 4 is a block diagram illustrating the image reading apparatus.

In FIG. 4, an analog/digital (A/D) converter (A/D) 55 is connected to the photomultiplier 31. The A/D 55 sequentially converts analog image signals which are sequentially output from the photomultiplier 31 at a predetermined time into digital image signals. The A/D 55 outputs the digital image signals to an image memory 56. The image memory 56 stores a digital image signal (fluorescence image) corresponding to one frame which is obtained by one scanning operation of the optical head 29 for the entire surface of the image carrier 13.

A communication unit 57 is connected to the image memory 56. The communication unit 57 is a USB communication interface and performs the communication of various kinds of data with the console 12. The communication unit 57 receives the fluorescence image from the image memory 56 and transmits the fluorescence image to the console 12.

The excitation light sources 26A to 26D, the optical head 29, the photomultiplier 31, the concave mirror 44, the substrate 46, and the filters 47A to 47E (filter unit 30) form a scanning unit 58 that is driven in order to output the fluorescence image of the image carrier 13. A controller 59 controls the overall operation of each unit, such as the scanning unit 58 or the communication unit 57. In particular, the scanning unit 58 performs scanning under the control of the controller 59.

The image reading apparatus 11 has two modes, that is, a normal mode and a maintenance mode. In the normal mode, the fluorescent light FL from the image carrier 13 is detected and a fluorescence image based on the detected fluorescent light FL is output. The normal mode is usually selected. In contrast, for example, the maintenance mode is selected when the image reading apparatus 11 starts every day.

Herein, shading is likely to occur in the fluorescence image. The shading is density unevenness that occurs in the entire fluorescence image. The shading is caused by the configuration of the image reading apparatus 11. Specifically, the shading is caused by a change in the length of the optical path of the fluorescent light FL which is caused by, for example, a change in the distance between the optical head 29 and the concave mirror 44 in the main scanning direction X, a change in the distance between the concave mirror 44 and the perforated concave mirror 43 in the sub-scanning direction Y, a variation in the distance between the substrate 46 and the concave mirror 44 in the sub-scanning direction Y, or a variation in the distance between the stage 25 and the optical head 29 (aspheric lens 51). In the maintenance mode, a reference image 86 (see FIG. 9) which is a reference for correcting the shading is acquired.

Figure 5:
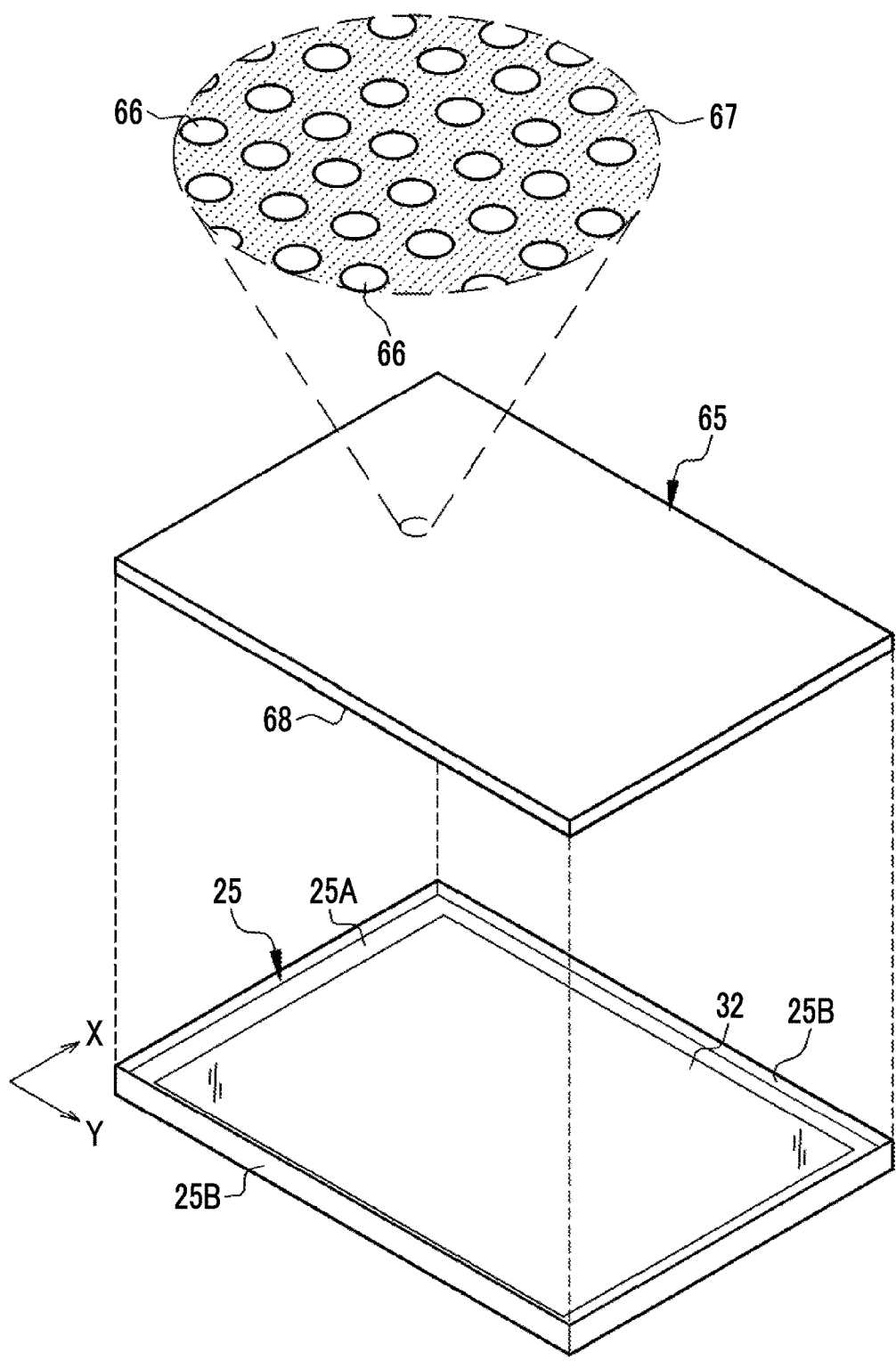
FIG. 5 is a perspective view illustrating a resin plate and a stage.

In FIG. 5, in the maintenance mode, instead of the image carrier 13, a resin plate 65 corresponding to a correction tool is set to the stage 25. Then, similarly to the image carrier 13, the optical head 29 scans the resin plate 65, detects the fluorescent light FL from the resin plate 65, and outputs the reference image 86 on the basis of the detected fluorescent light FL.

The resin plate 65 includes an organic fluorescent material having the wavelength characteristic that the wavelength bands of an excitation wavelength and an emission wavelength at least partially overlap the wavelength bands of the excitation wavelength and the emission wavelength of the fluorescent material included in the image carrier 13. In the resin plate 65, the organic fluorescent material is uniformly dispersed by a binder which is an organic material, which will be described below. Therefore, uniform fluorescent light FL is emitted from the entire resin plate 65. That is, in a case in which the resin plate 65 is irradiated with the excitation light EL having the same wavelength band as that emitted to the image carrier 13, the fluorescent light FL having the same wavelength band as that emitted from the fluorescent material included in the image carrier 13 is uniformly emitted from the entire resin plate 65.

The resin plate 65 has a size that covers the entire scanning region of the optical head 29 is held by the stage 25. Here, the size that covers the entire scanning region of the optical head 29 means that the plane size of the resin plate 65 is equal to or less than the plane size of the stage 25 and is equal to or greater than the plane size of the glass plate 32 and is large enough to cover at least the entire glass plate 32 that delimits the scanning region of the optical head 29. As described above, the glass plate 32 has a plane size that is slightly less than the plane size of the bottom 25A of the stage 25. Therefore, when the plane size of the resin plate 65 is equal to or less than the plane size of the stage 25 and is equal to or greater than the plane size of the glass plate 32, the resin plate 65 can be set to the stage 25 to cover the entire glass plate 32.

As illustrated in an ellipse represented by a dashed line in which a portion of the resin plate 65 is enlarged and displayed, the resin plate 65 includes an organic fluorescent material 66 and a binder 67 in which the organic fluorescent material 66 is dispersed. The binder 67 is any one of a vinyl chloride resin, a polycarbonate resin, a methacrylic resin, a silicone resin, and a polyacrylamide resin. The resin plate 65 is obtained by mixing the organic fluorescent material 66 with the resin solution, uniformly dispersing the organic fluorescent material 66, and pouring the solution in a plate-shaped mold, and solidifying the solution.

When the resin plate 65 is set to the stage 25, a roughening process is performed for the surface (excitation light scanning surface) 68 of the resin plate 65 that comes into contact with the glass plate 32 of the stage 25. The roughening process is performed using any one of a solvent, fine particle powder, and a pressure die.

In general, the roughening process using the solvent is generally called etching and applies the solvent onto the surface 68 or immerses the surface 68 in the solvent to roughen the surface 68. The roughening process using the fine particle powder is generally called blast and sprays the fine particle powder to the surface 68 to roughen the surface 68. The roughening process using the pressure die is generally called press and presses, for example, a pressure die having an embossed irregular fine pattern against the surface 68 to roughen the surface 68.

Figures 6, 7:
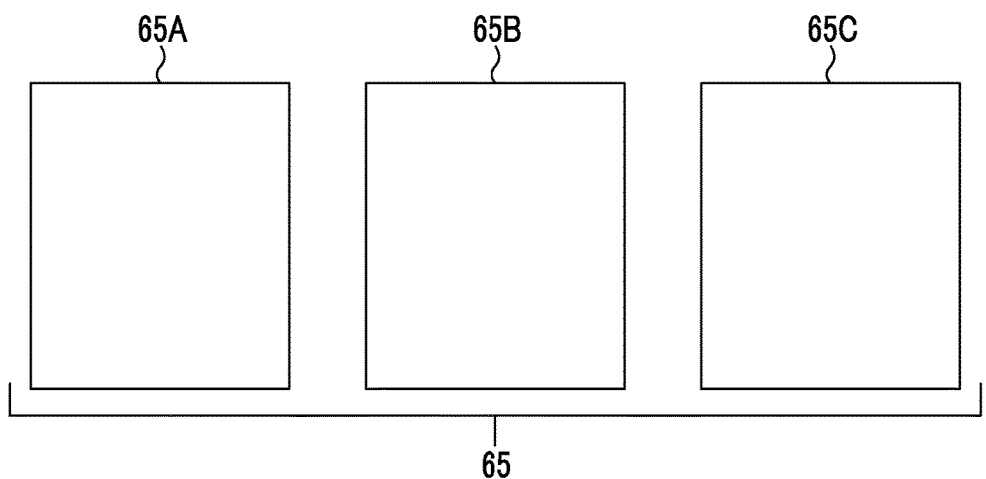
FIG. 6 is a plan view illustrating first to third resin plates.
FIG. 7 is a table illustrating organic fluorescent materials, excitation wavelengths, and emission wavelengths of the first resin plate and the second resin plate.

As illustrated in FIG. 6, the resin plate 65 includes a first resin plate 65A, a second resin plate 65B, and a third resin plate 65C. The first resin plate 65A corresponds to a first correction tool and is used for infrared excitation light with a center wavelength of 770 nm to 800 nm. The second resin plate 65B corresponds to a second correction tool and is used for red excitation light with a center wavelength of 650 nm to 690 nm. The third resin plate 65C is used for green excitation light with a center wavelength of 520 nm to 540 nm and blue excitation light with a center wavelength of 460 nm to 490 nm.

The third resin plate 65C is the same as the correction tool disclosed in JP2003-315944A and is, for example, a vinyl chloride resin plate (product name: KYDAC, part number: KDN1275, color tone: sun valley beige) manufactured by Sumitomo Bakelite Co., Ltd. In addition, a resin plate including an inorganic fluorescent material, such as YAG:Ce disclosed in JP1999-355568A (JP-H11-355568A), may be used as the third resin plate 65C. Next, the first resin plate 65A and the second resin plate 65B according to the invention will be described in detail except the third resin plate 65C.

A table 70 illustrated in FIG. 7 illustrates the organic fluorescent materials 66, excitation wavelengths, and emission wavelengths of the first resin plate 65A and the second resin plate 65B. In the case of the first resin plate 65A, the organic fluorescent material 66 is a phthalocyanine-based pigment. In the case of the second resin plate 65B, the organic fluorescent material 66 is an anthraquinone-based pigment. As described above, in the case of the first resin plate 65A, the excitation wavelength is in the range of 770 nm to 800 nm (infrared excitation light). In the case of the second resin plate 65B, the excitation wavelength is in the range of 625 nm to 645 nm and in the range of 650 nm to 690 nm (red excitation light). In the case of the first resin plate 65A, the emission wavelength is 845 nm (infrared fluorescent light). In the case of the second resin plate 65B, the emission wavelength is 720 nm (red fluorescent light). In addition, the emission wavelength indicates a peak wavelength which is the maximum intensity wavelength of the emission spectrum of fluorescent light of each color.

For example, a phthalocyanine compound disclosed in J51993-131750A (JP-H05-131750A) and WO2012/102395A can be used as the phthalocyanine-based pigment which is the organic fluorescent material 66 of the first resin plate 65A. Specifically, the phthalocyanine-based pigment is a tin phthalocyanine (phthalocyanine tin complex) pigment in which tin is disposed at the center of a phthalocyanine ring. In addition, the phthalocyanine-based pigment is a copper phthalocyanine (phthalocyanine copper complex) pigment in which copper is disposed at the center of a phthalocyanine ring. For example, "Pigment Green 36" represented by Expression (A) and "Pigment Green 7" represented by Expression (B) may be used. It is preferable to use the tin phthalocyanine pigment.

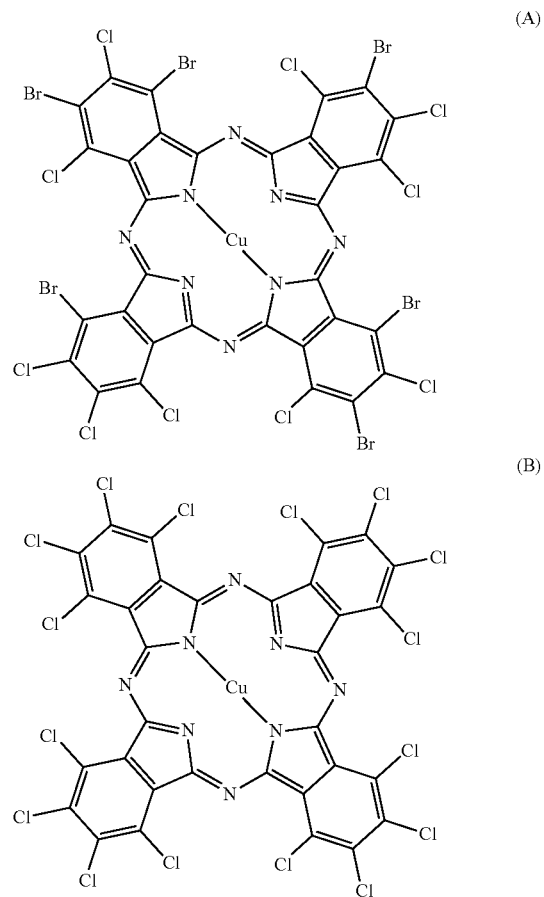

For example, "Solvent Blue 35" represented by Expression (C) and "Solvent Blue 36" represented by Expression (D) can be used as the anthraquinone-based pigment which is the organic fluorescent material 66 of the second resin plate 65B.

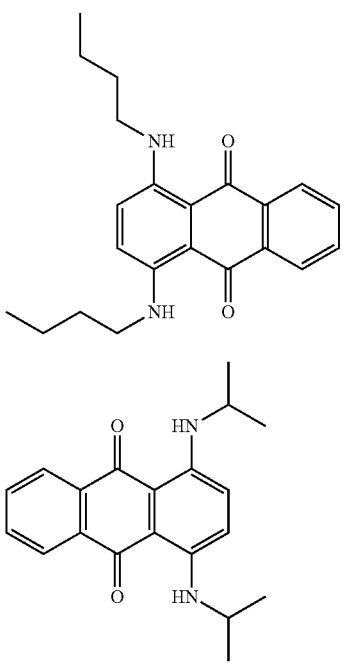

(C)

(D)

The first resin plate 65A and the second resin plate 65B may be commercially available resin plates. For example, a vinyl chloride resin plate (product name: TAKISHARON (new product name: NEW TAKISHARON), product category: TSLa (new product category: TSLA), part number: W7087 (new part number: W4066), color tone: green) manufactured by Takiron Co., Ltd. (new company name: C. I. TAKIRON Corporation) or a vinyl chloride resin plate (product name: TAKISHARON (new product name: NEW TAKISHARON), product category: TSLaND (new product category: TSLAND), part number: N7087 (new part number: N4066), color tone: green) manufactured by Takiron Co., Ltd. (new company name: C. I. TAKIRON Corporation) can be used as the first resin plate 65A. For example, a vinyl chloride resin plate (product name: TAKISHARON (new product name: NEW TAKISHARON), product category: TSLa (new product category: TSLA), part number: W5567 (new part number: W502), color tone: blue) manufactured by Takiron Co., Ltd. (new company name: C. I. TAKIRON Corporation) or a vinyl chloride resin plate (product name: TAKISHARON (new product name: NEW TAKISHARON), product category: TSLaND (new product category: TSLAND), part number: N5567 (new part number: N502), color tone: blue) manufactured by Takiron Co., Ltd. (new company name: C. I. TAKIRON Corporation) can be used as the second resin plate 65B.

The second resin plate 65B is excited by red excitation light with a wavelength of 625 nm to 645 nm, in addition to red excitation light with a wavelength of 650 nm to 690 nm, and emits red fluorescent light. Therefore, even in a case in which the red excitation light source 26B emits red excitation light with a center wavelength of 625 nm to 645 nm, for example, a center wavelength of 635 nm, it is possible to use the second resin plate 65B in order to correct shading.

Figure 8:
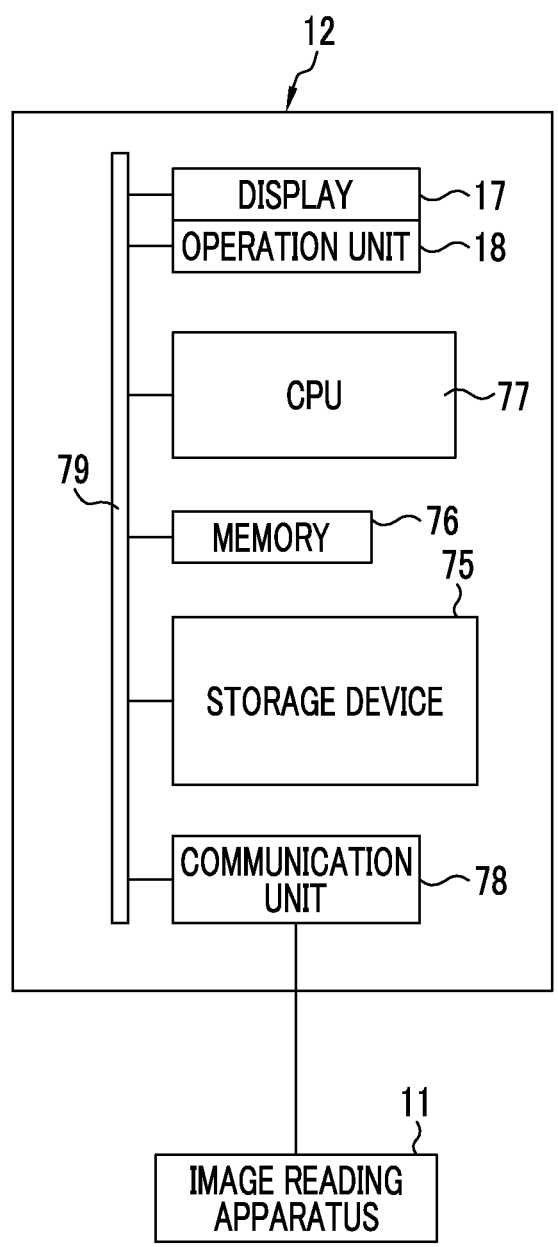
FIG. 8 is a block diagram illustrating a console.

In FIG. 8, the console 12 comprises a storage device 75, a memory 76, a central processing unit (CPU) 77, and a communication unit 78, in addition to the display 17 and the operation unit 18. These units are connected to each other through a data bus 79.

The storage device 75 is a hard disk drive that is provided in the console 12 or is connected through a cable or a network or a disk array obtained by connecting a plurality of hard disk drives. The storage device 75 stores, for example, a control program, such as an operating system, various application programs, and various kinds of data associated with these programs.

The memory 76 is a work memory that is used to perform a process by the CPU 77. The CPU 77 loads a program stored in the storage device 75 to the memory 76 and performs a process based on the program to control the overall operation of each unit of the console 12. The communication unit 78 is a USB communication interface that performs the communication of various kinds of data with the image reading apparatus 11, similarly to the communication unit 57 of the image reading apparatus 11.

Figure 9:
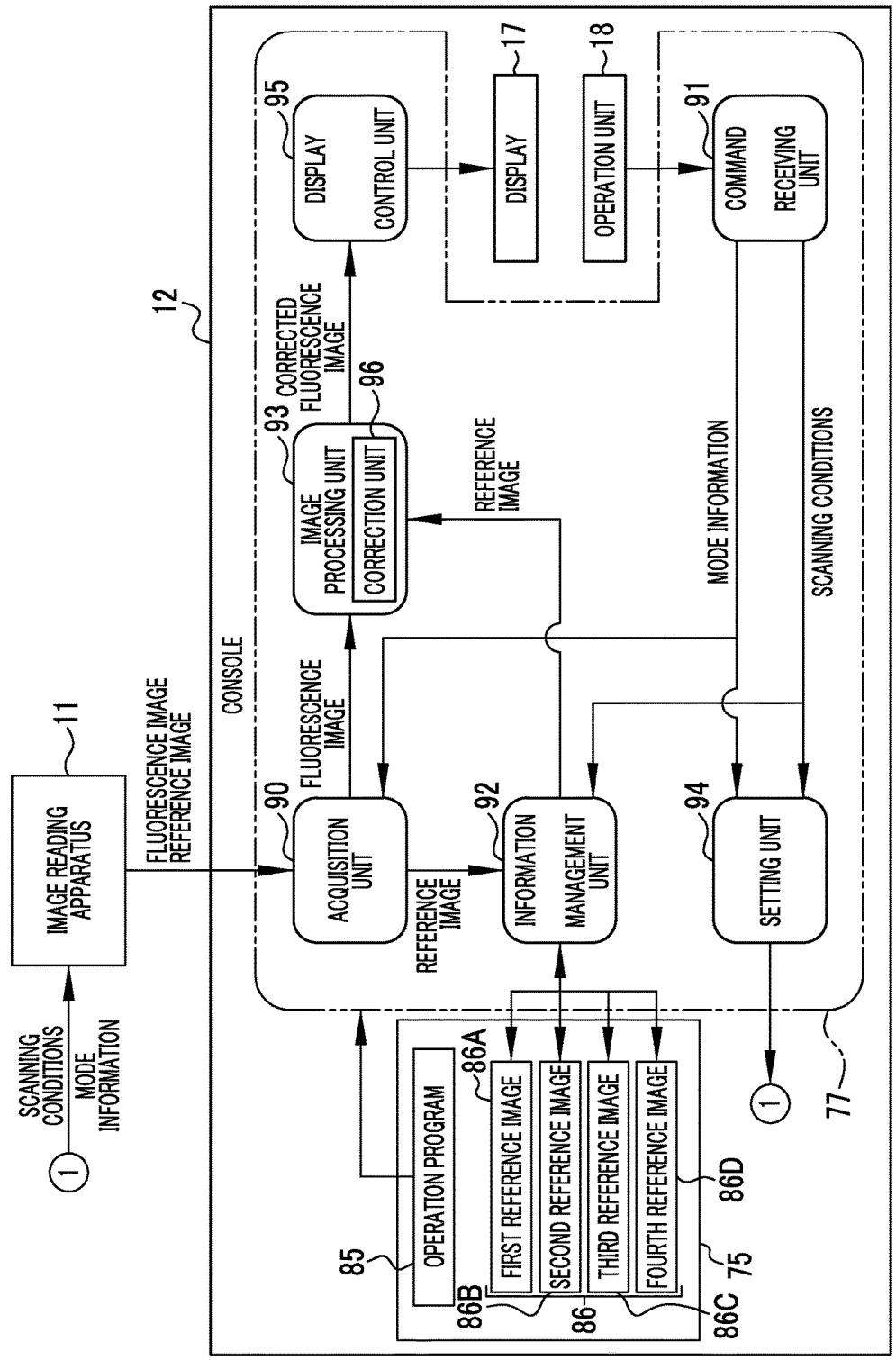
FIG. 9 is a block diagram illustrating a CPU of the console.

In FIG. 9, the storage device 75 stores an operation program 85. The operation program 85 is an application program that causes the console 12 to function as a shading correction apparatus.

The storage device 75 stores the reference image 86, in addition to the operation program 85. The reference image 86 includes a first reference image 86A for infrared excitation light which is obtained using the first resin plate 65A, a second reference image 86B for red excitation light which is obtained using the second resin plate 65B, and a third reference image 86C for green excitation light and a fourth reference image 86D for blue excitation light which are obtained using the third resin plate 65C.

When the operation program 85 starts, the CPU 77 functions as an acquisition unit 90, a command receiving unit 91, an information management unit 92, an image processing unit 93, a setting unit 94, and a display control unit 95 in cooperation with the memory 76. A correction unit 96 is constructed in the image processing unit 93.

The acquisition unit 90 has an acquisition function of acquiring a fluorescence image and the reference image 86 from the image reading apparatus 11. The acquisition unit 90 outputs the fluorescence image to the image processing unit 93 and outputs the reference image 86 to the information management unit 92.

The command receiving unit 91 receives an operation command input from the operation unit 18. Examples of the operation command include a mode selection command to select one of the normal mode and the maintenance mode and a scanning condition setting command to set the scanning conditions of the fluorescence image.

The scanning conditions include, for example, a set of the excitation light source 26 used and the filter 47, the voltage value of the photomultiplier 31, and the resolution of the fluorescence image. The voltage value of the photomultiplier 31 can be changed to change the density of the fluorescence image. The resolution of the fluorescence image is, specifically, an interval (pixel pitch) at which the fluorescent light FL is read and the scanning speed of the optical head 29 which determine the resolution of the fluorescence image. The command receiving unit outputs information (hereinafter, referred to as mode information) of the mode selected by the mode selection command to the acquisition unit 90 and the setting unit 94 and outputs the scanning conditions set by the scanning condition setting command to the information management unit 92 and the setting unit 94. Examples of the operation command include a command (hereinafter, referred to as a scanning execution command) to instruct the image reading apparatus 11 to perform scanning, in addition to the above-mentioned commands.

In a case in which the mode indicated by the mode information from the command receiving unit 91 is the normal mode, the acquisition unit 90 recognizes the image from the image reading apparatus 11 as the fluorescence image and transmits the image to the image processing unit 93. In contrast, in a case in which the mode indicated by the mode information from the command receiving unit 91 is the maintenance mode, the acquisition unit 90 recognizes the image from the image reading apparatus 11 as the reference image 86 and transmits the image to the information management unit 92.

The information management unit 92 manages various kinds of information stored in the storage device 75. The information management unit 92 stores the reference image 86 transmitted from the acquisition unit 90 in the storage device 75. In addition, the information management unit 92 reads the reference image 86 corresponding to the excitation light source 26 that uses the scanning conditions from the command receiving unit 91 from the storage device 75 and transmits the read reference image 86 to the image processing unit 93. For example, in a case in which the excitation light source 26 used is the infrared excitation light source 26A, the information management unit 92 transmits the first reference image 86A for infrared excitation light to the image processing unit 93. In a case in which the excitation light source 26 used is the red excitation light source 26B, the information management unit 92 transmits the second reference image 86B for red excitation light to the image processing unit 93.

The correction unit 96 of the image processing unit 93 has a correction function of performing a shading correction process for the fluorescence image from the acquisition unit 90 on the basis of the reference image 86 from the information management unit 92. Specifically, in a case in which the density of the fluorescence image from the acquisition unit 90 is FR, the density of the reference image 86 from the information management unit 92 is FF, the density of a dark image obtained by performing scanning with the optical head 29, without emitting excitation light is FD, and the density of a shading-corrected fluorescence image (hereinafter, referred to as a corrected fluorescence image) is FC, the correction unit 96 performs calculated represented by Expression (1):

$$FC=(FR-FD)/(FF-FD) \quad (1).$$

In a case in which dark noise or the offset of an image signal is so small as to be negligible, shading correction may be performed using Expression (2):

$$FC=FR/FF \quad (2).$$

The calculation represented by Expression (1) may be performed for each pixel forming the fluorescence image, the reference image 86, and the dark image or may be performed for a plurality of regions obtained by dividing the fluorescence image, the reference image 86, and the dark image, for example, each row arranged in the main scanning direction X. In a case in which the calculation is performed for each region, the representative value (for example, the average value or the mode) of the density of each region of the fluorescence image, the reference image 86, and the dark image is substituted into Expression (1). This holds for Expression (2).

The image processing unit 93 performs various kinds of image processing, such as a pixel interpolation process, a color correction process, and a gradation process, for the fluorescence image, in addition to the shading correction. The correction unit 96 performs shading correction before other kinds of image processing. The image processing unit 93 outputs the corrected fluorescence image to the display control unit 95.

The setting unit 94 sets the mode information and the scanning conditions from the command receiving unit 91 in the image reading apparatus 11. In the image reading apparatus 11, the mode is switched on the basis of the mode information from the setting unit 94. In addition, the scanning conditions from the setting unit 94 are set in various drivers of the scanning unit 58, such as a driver of the excitation light source 26, drivers of motors for moving the optical head 29, the substrate 46, the concave mirror 44, and the filter unit, and a driver of the photomultiplier 31. In the maintenance mode, the scanning conditions input by the operation unit 18 are not set, but the scanning conditions for the maintenance mode which have been stored in the storage device 75 in advance are set.

The display control unit 95 controls the display output of the corrected fluorescence image from the image processing unit 93. Specifically, the display control unit 95 generates a screen for displaying the corrected fluorescence image and outputs the screen to the display 17. Examples of the screen include a mode selection screen, a scanning condition setting screen, and a screen for instructing the execution of scanning.

Figure 10:
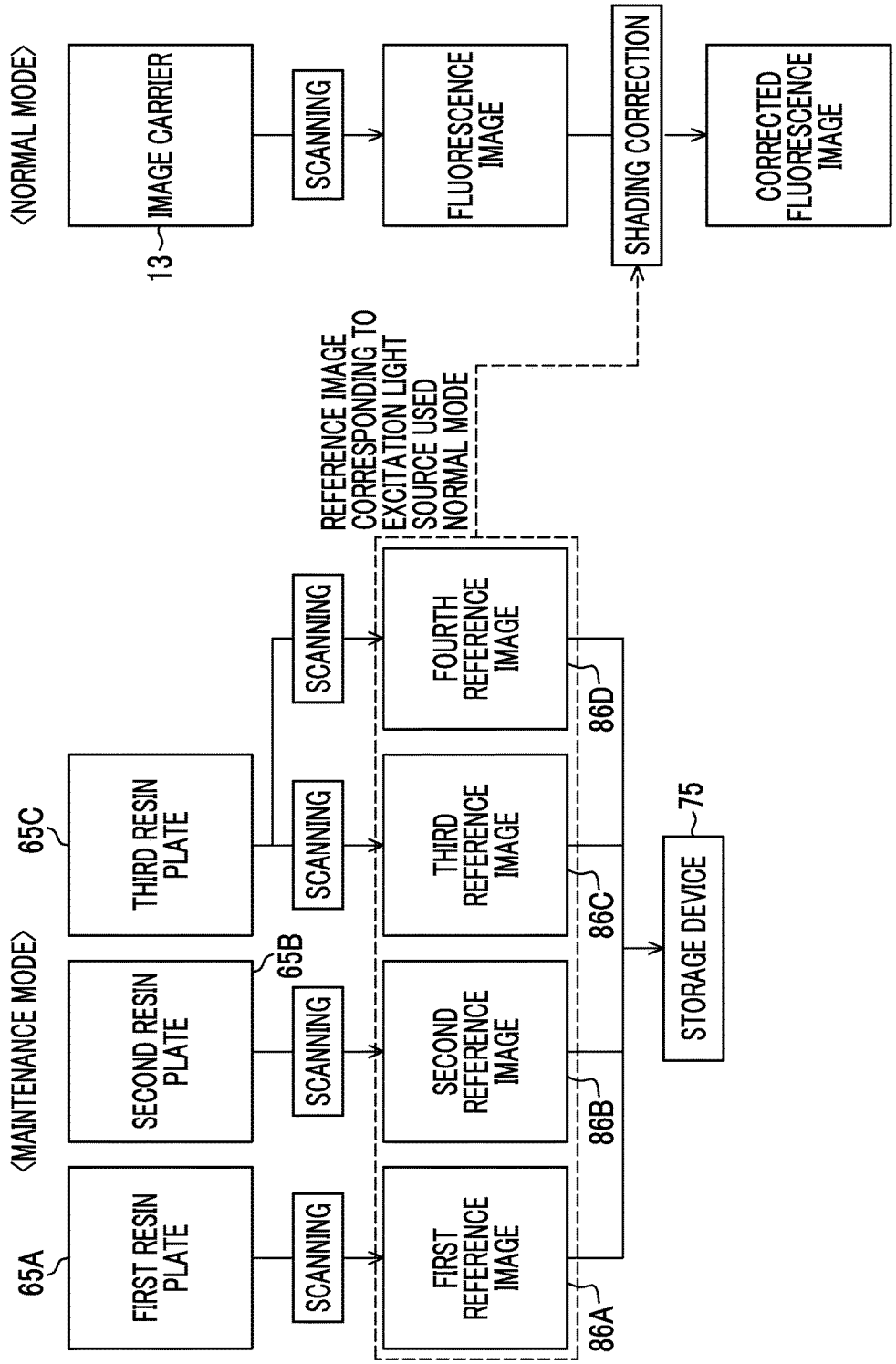
FIG. 10 is a diagram schematically illustrating a procedure in each mode.

As illustrated on the left side of FIG. 10, in the maintenance mode, the first resin plate 65A is scanned with the infrared excitation light source 26A and the first reference image 86A is output. In addition, the second resin plate 65B is scanned with the red excitation light source 26A and the second reference image 86B is output. The third resin plate 65C is scanned with the green excitation light source 26C and the blue excitation light source 26D and the third reference image 86C and the fourth reference image 86D are output. Then, the reference images 86A to 86D are stored in the storage device 75.

In contrast, as illustrated on the right side of FIG. 10, in the normal mode, the image carrier 13 is scanned with the excitation light source 26 set in the scanning conditions and a fluorescence image is output. Then, shading correction is performed for the fluorescence image on the basis of the reference image corresponding to the used excitation light source 26 and a corrected fluorescence image is output.

Figure 11:
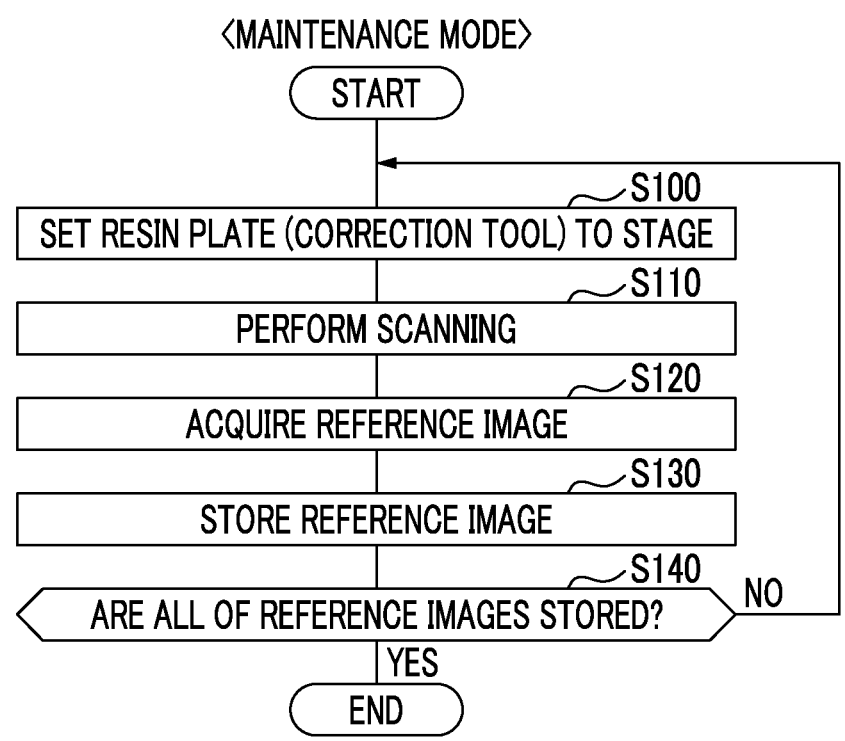
FIG. 11 is a flowchart illustrating a procedure in a maintenance mode.

Next, the operation of the above-mentioned configuration will be described with reference to the flowcharts illustrated in FIGS. 11 and 12. First, in FIG. 11, the user operates the operation unit 18 to select the maintenance mode. First, the first resin plate 65A is set to the stage 25 (Step S100). After the first resin plate 65A is set, the user inputs a scanning execution command through the screen displayed on the display 17. Then, the image reading apparatus 11 scans the first resin plate 65A using the infrared excitation light source 26A (the infrared filter 47A is used as the filter 47) (Step S110).

The first reference image 86A is output from the image reading apparatus 11 by the scanning of the first resin plate 65A by the infrared excitation light source 26A. The acquisition unit 90 of the console 12 acquires the first reference image 86A (Step S120; an acquisition step). The first reference image 86A is output from the acquisition unit 90 to the information management unit 92 and is then stored in the storage device 75 (Step S130).

Then, the user sets the second resin plate 65B to the stage 25 and finally sets the third resin plate 65C to the stage 25. A series of processes in Steps S110 to S130 is similarly performed for the second resin plate 65B and the third resin plate 65C. Specifically, the second resin plate 65B is scanned with the red excitation light source 26B (the red filter 47B is used as the filter 47) and the third resin plate 65C is scanned with the green excitation light source 26C and the blue excitation light source 26D (the green filter 47C and the blue filter 47D are used as the filter 47). Then, the second reference image 86B, the third reference image 86C, and the fourth reference image 86D are acquired by the acquisition unit 90 and are then stored in the storage device 75. In a case in which all of the reference images 86A to 86D are stored in the storage device 75 (YES in Step S140), the maintenance mode ends.

The first resin plate 65A includes a phthalocyanine-based pigment which is the organic fluorescent material 66 that is excited by infrared excitation light with a center wavelength of 770 nm to 800 nm and emits infrared fluorescent light with a peak wavelength of 845 nm. The second resin plate 65B includes an anthraquinone-based pigment which is the organic fluorescent material 66 that is excited by red excitation light with a center wavelength of 650 nm to 690 nm and emits red fluorescent light with a peak wavelength of 720 nm. Therefore, shading correction can be performed on the basis of the first reference image 86A and the second reference image 86B which are obtained by irradiating the first resin plate 65A and the second resin plate 65B with excitation light having a center wavelength greater than 650 nm.

The second resin plate 65B is excited by red excitation light with a center wavelength of 625 nm to 645 nm, in addition to red excitation light with a center wavelength of 650 nm to 690 nm, and emits red fluorescent light. Therefore, the second resin plate 65B can also be used for shading correction in a case in which the red excitation light source 26B emits red excitation light with a center wavelength of 625 nm to 645 nm, for example, a center wavelength of 635 nm.

Since an inorganic fluorescent material is not used, but the organic fluorescent material 66 is used as the fluorescent material, it is possible to achieve the required characteristic of the correction tool that emits uniform fluorescent light from the entire surface with high reproducibility. Therefore, it is possible to accurately perform shading correction, particularly, shading correction in a case in which excitation light with a center wavelength greater than 650 nm is used.

A phthalocyanine-based pigment is used as the organic fluorescent material 66 of the first resin plate 65A and an anthraquinone-based pigment is used as the organic fluorescent material 66 of the second resin plate 65B. The phthalocyanine-based pigment and the anthraquinone-based pigment are popular pigments and are likely to be easily obtained at a lower price than a fluorescent pigment that is used for the fluorescent labeling of a biological material. Therefore, it is possible to form the first resin plate 65A and the second resin plate 65B at a low cost. In addition, the phthalocyanine-based pigment and the anthraquinone-based pigment have higher resistance to discoloration and higher durability against long-term use and repeated use than the fluorescent pigment that is used for the fluorescent labeling of a biological material.

The first resin plate 65A and the second resin plate 65B are obtained by dispersing the organic fluorescent material 66 in the binder 67 and solidifying the binder 67. Therefore, it is more easy to handle the first resin plate 65A and the second resin plate 65B than, for example, a flexible sheet.

The binder 67 is any one of a vinyl chloride resin, a polycarbonate resin, a methacrylic resin, a silicone resin, and a polyacrylamide resin. These resins are well known and have high affinity with the organic fluorescent material 66. Therefore, it is possible to simply form the first resin plate 65A and the second resin plate 65B in which the organic fluorescent material 66 is uniformly dispersed.

The first resin plate 65A and the second resin plate 65B have a size that cover the entire scanning region of the optical head 29. Therefore, it is possible to perform shading correction that covers the entire scanning region of the optical head 29. In contrast, in a case in which the first resin plate 65A and the second resin plate 65B have a size that covers a portion of the scanning region of the optical head 29, it is necessary to perform scanning several times while changing the position of the first resin plate 65A and the second resin plate 65B. Therefore, the above-mentioned structure makes it possible to save the time and effort to repeat the scanning.

A roughening process is performed for the surface 68 of the resin plate 65 which comes into contact with the glass plate 32 of the stage 25. Since light is scattered at the boundary between the glass plate 32 and the surface 68 by the roughening process, the generation of a Newton ring (interference fringe) is prevented. The Newton ring is noise that is unnecessary to generate the reference image 86. Therefore, when the generation of the Newton ring is prevented by the roughening process, it is possible to perform accurate shading correction. In this embodiment, the roughening process is performed for only the surface 68. However, the roughening process may also be performed for a surface opposite to the surface 68 such that the front and rear surfaces can be used without any distinction.

Figure 12:
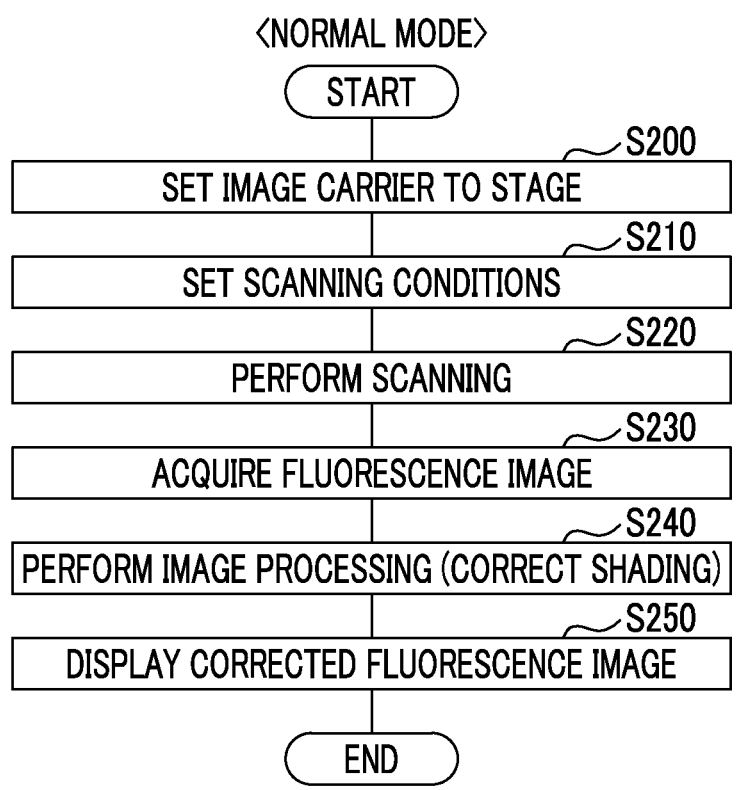
FIG. 12 is a flowchart illustrating a procedure in a normal mode.

In a case in which the image carrier 13 is scanned, the user operates the operation unit 18 to select the normal mode, as illustrated in FIG. 12. In the normal mode, the resin plate 65 is removed and the image carrier 13 is set to the stage 25 (Step S200). After the image carrier 13 is set, the user inputs a scanning condition setting command and a scanning execution command through the screen displayed on the display 17. Then, scanning conditions are set in the image reading apparatus 11 (Step S210) and scanning is performed on the basis of the scanning conditions (Step S220).

A fluorescence image is output from the image reading apparatus 11 by the scanning of the image carrier 13. The fluorescence image is acquired by the acquisition unit 90 of the console 12 (Step S230). The fluorescence image is output from the acquisition unit 90 to the image processing unit 93.

The reference image 86 corresponding to the excitation light source 26 used for the scanning is transmitted from the information management unit 92 to the correction unit 96 of the image processing unit 93. The correction unit 96 performs shading correction for the fluorescence image from the acquisition unit 90 on the basis of the reference image 86 from the information management unit 92 (Step S240; a correction step).

The use of Expression (1) for shading correction means that shading correction is performed after the density FD of a dark image is subtracted from the density FR of the fluorescence image and the density FF of the reference image 86 to remove dark noise or image signal offset from the fluorescence image and the reference image 86. As such, when shading correction is performed after dark noise or image signal offset is removed, it is possible to guarantee the accuracy of correction.

Various kinds of image processing are performed for the corrected fluorescence image which is a shading-corrected fluorescence image and the corrected fluorescence image is output to the display control unit 95. The corrected fluorescence image is displayed on the display 17 by the display control unit 95 (Step S250). In this way, one scanning operation ends.

Second Embodiment

In the first embodiment, the first resin plate 65A and the second resin plate 65B are separately provided. However, as in a second embodiment illustrated in FIGS. 13 to 15, the first resin plate 65A and the second resin plate 65B may be integrated with each other.

Figure 13:
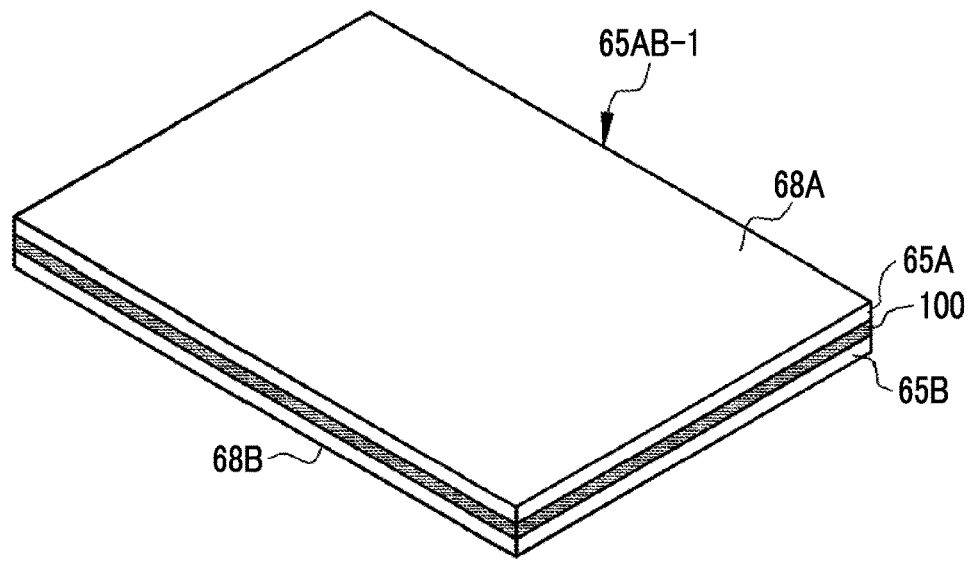
FIG. 13 is a diagram illustrating a resin plate obtained by interposing a black plate between the first resin plate and the second resin plate and integrating the plates.

A resin plate 65AB-1 illustrated in FIG. 13 is obtained by integrating the first resin plate 65A and the second resin plate 65B, with a black plate 100 interposed between the first resin plate 65A and the second resin plate 65B. The black plate 100 is, for example, an aluminum plate subjected to a black alumite treatment and has the same plane size as the first resin plate 65A and the second resin plate 65B.

The surface 68A of the first resin plate 65A and the surface 68B of the second resin plate 65B are opposite to a bonding surface of the black plate 100. The roughening process is performed for the surfaces 68A and 68B, as in the first embodiment.

First, the resin plate 65AB-1 is set such that the surface 68A of the first resin plate 65A comes into contact with the glass plate 32 and is scanned with the infrared excitation light source 26A. Then, the resin plate 65AB-1 is removed from the image reading apparatus 11, is reversed, is set such that the surface 68B of the second resin plate 65B comes into contact with the glass plate 32, and is scanned with the red excitation light source 26B. As such, since the first resin plate 65A and the second resin plate 65B are integrated with each other, it is easy to hand the resin plates. In addition, it is possible to reduce the number of resin plates 65.

Figure 14:
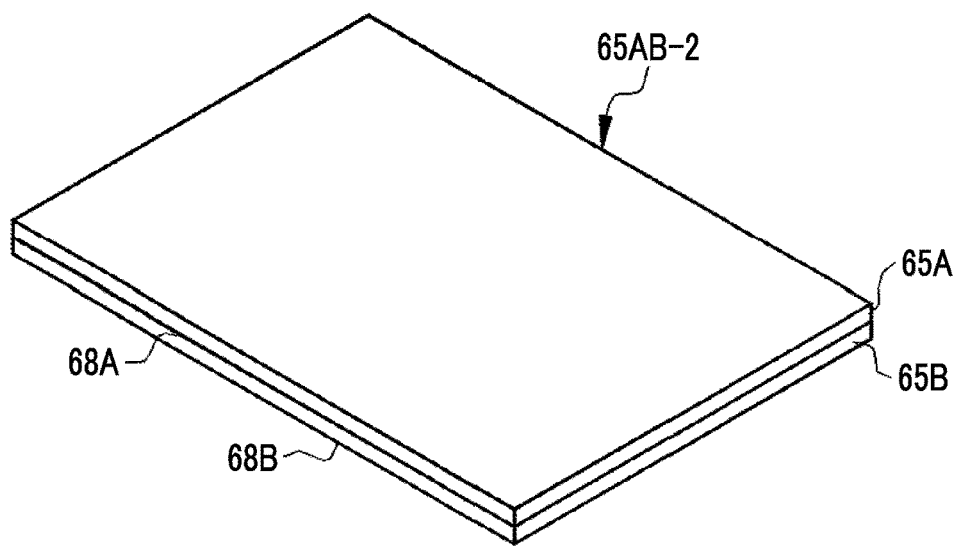
FIG. 14 is a diagram illustrating a resin plate obtained by directly bonding the first resin plate and the second resin plate and integrating the plates.

A resin plate 65AB-2 illustrated in FIG. 14 is obtained by directly bonding the first resin plate 65A and the second resin plate 65B using, for example, an adhesive, without interposing the black plate 100 therebetween, such that first resin plate 65A and the second resin plate 65B are integrated with each other. In this case, the surface 68A of the first resin plate 65A is a bonding surface to the second resin plate 65B and the surface 68B of the second resin plate 65B is opposite to the bonding surface to the first resin plate 65A. In this case, the roughening process is performed for only the surface 68B, as in the first embodiment.

Figure 15:
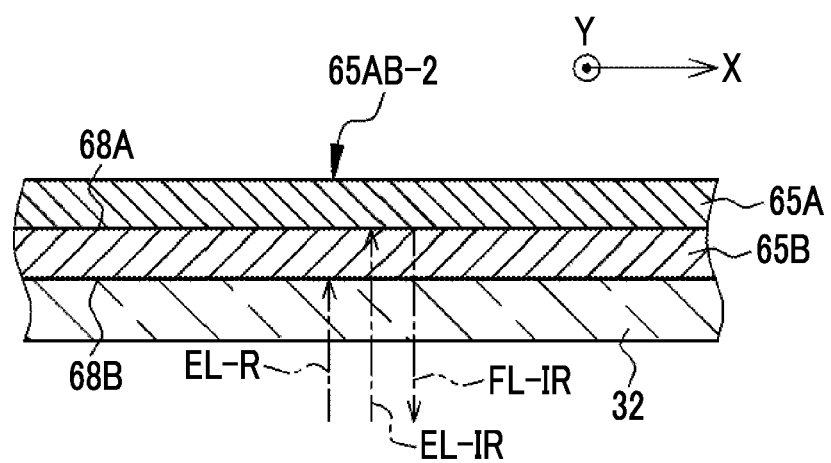
FIG. 15 is a diagram illustrating the usage state of the resin plate illustrated in FIG. 14.

As illustrated in FIG. 15, the resin plate 65AB-2 is set such that the surface 68B of the second resin plate 65B comes into contact with the glass plate 32. The second resin plate 65B which is a vinyl chloride resin plate manufactured by Takiron Co., Ltd. described in the first embodiment has the wavelength characteristic that it does not transmit red excitation light represented by letters EL-R and transmits infrared excitation light represented by letters EL-IR and infrared fluorescent light represented by letters FL-IR. Therefore, infrared excitation light is transmitted through the second resin plate 65B and is emitted to the surface 68A of the first resin plate 65A and infrared fluorescent light is transmitted through the second resin plate 65B and is acquired by the optical head.

Therefore, in a case in which the resin plate 65AB-2 is used, unlike the resin plate 65AB-1 illustrated in FIG. 12, it is not necessary to extract the resin plate from the image reading apparatus 11 and to reverse the resin plate. It is possible to continuously perform a scanning operation using the infrared excitation light source 26A and a scanning operation using the red excitation light source 26B. In addition, it is easy to handle the resin plate.

However, in this case, the length of the optical path of the infrared excitation light and the infrared fluorescent light is changed by a value corresponding to the transmission of light through the second resin plate 65B, as compared to the case in which only the first resin plate 65A is used. Therefore, the focal depth of the optical head 29 is set to a value that is so large that a change in the length of the optical path of the infrared excitation light and the infrared fluorescent light is negligible. A material having the wavelength characteristic that it transmits the infrared excitation light and the infrared fluorescent light is used as the adhesive for bonding the first resin plate 65A and the second resin plate 65B.

Figure 16:
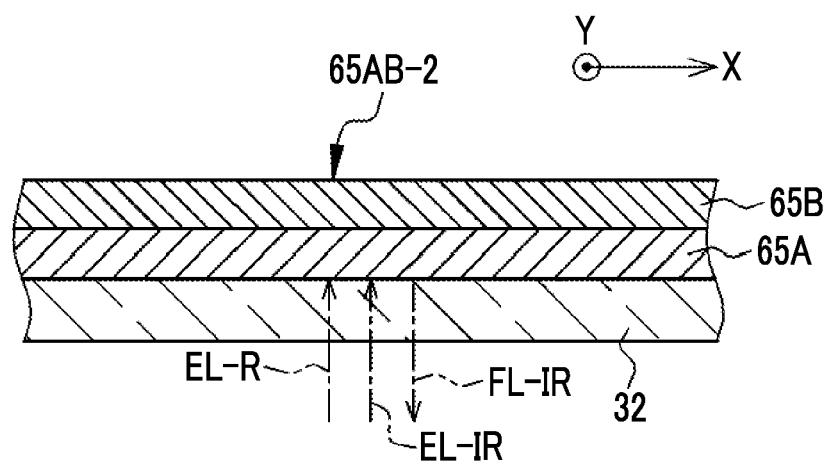
FIG. 16 is a diagram illustrating a state in which the resin plate is set in a direction opposite to that illustrated in FIG. 15.

The first resin plate 65A described in the first embodiment has the wavelength characteristic that it does not transmit the red excitation light represented by letters EL-R. Therefore, contrary to the case illustrated in FIG. 15, when the resin plate 65AB-2 is set such that the first resin plate 65A comes into contact with the glass plate 32 as illustrated in FIG. 16, it is possible to obtain the first reference image 86A for infrared excitation light. However, it is difficult to obtain the second reference image 86B for red excitation light. In this case, for this reason, the resin plate 65AB-2 is extracted from the image reading apparatus 11 and is reversed. Therefore, in a case in which the resin plate 65AB-2 is used, the user needs to pay attention to the direction in which the resin plate 65AB-2 is set to the stage 25. For this reason, it is preferable to put, for example, marks indicating the front and rear sides on the resin plate 65AB-2.

Third Embodiment

In each of the above-described embodiments, the resin plate 65 which is a correction tool has a size that covers the entire scanning region of the optical head 29. However, as in a third embodiment illustrated in FIG. 17, the correction tool may be a cap type.

Figure 17:
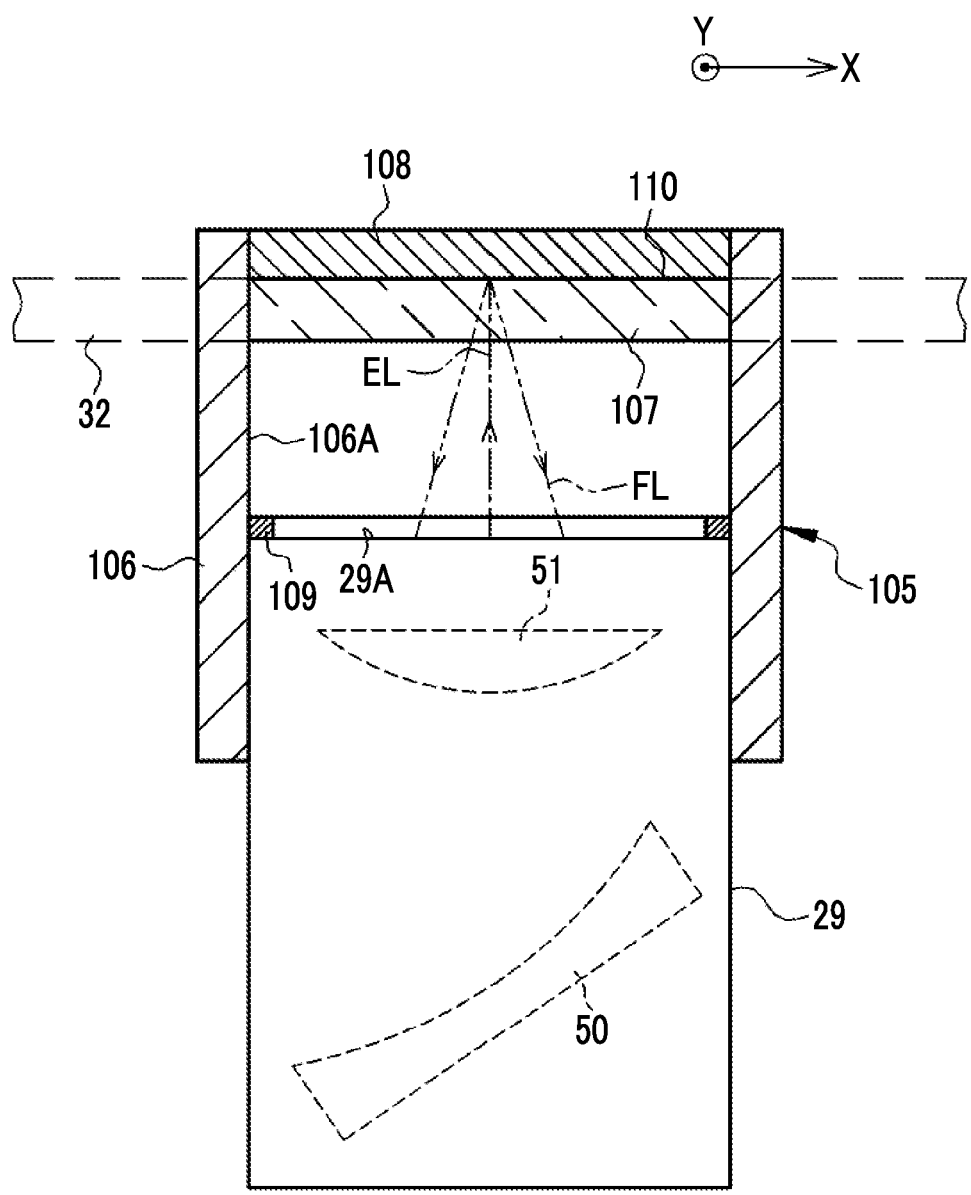
FIG. 17 is a diagram illustrating the usage state of a cap-type correction tool.

In FIG. 17, a correction tool 105 according to this embodiment is a cap type that is detachable from the optical head 29. The correction tool 105 includes a main body 106, a glass plate 107, and a resin plate 108.

The main body 106 has an inner circumferential surface 106A having a size that is equal to or slightly larger than the size of an upper surface 29A of the optical head 29 facing the stage 25. A stopper 109 that defines the mounting position of the correction tool 105 is provided on the inner circumferential surface 106A.

The glass plate 107 is made of the same material as that the glass plate 32 of the stage 25 and has the same thickness as the glass plate 32. The resin plate 108 is one of the first resin plate 65A and the second resin plate 65B, the resin plate 65AB-1 illustrated in FIG. 13, or the resin plate 65AB-2 illustrated in FIG. 14. The same roughening process as that in the first embodiment is performed for a surface 110 of the resin plate 108 which comes into contact with the glass plate 107.

In a case in which the correction tool 105 is used, first, the stage 25 is removed. Then, the correction tool 105 is inserted into the optical head 29 such that the stopper 109 comes into contact with the upper surface 29A of the optical head 29 and is fixed, as illustrated in FIG. 17. In this case, the distance between the upper surface 29A and the glass plate 107 is equal to the distance between the upper surface 29A and the glass plate 32. After the correction tool 105 is mounted, the optical head 29 irradiates the resin plate 108 with excitation light to scan the resin plate 108 while being moved, as in each of the above-described embodiments.

In the third embodiment using the cap-type correction tool 105 that is detachable from the optical head 29, it is assumed that the accuracy of the mechanical dimensions of the entire stage 25 is within an allowable range and a variation in the distance between the stage 25 and the optical head 29 (aspheric lens 51) is so small as to be negligible. Therefore, in the third embodiment, shading caused by a change in the length of the optical path except the variation in the distance between the stage 25 and the optical head 29 (aspheric lens 51) is corrected.

According to the cap-type correction tool 105 that is detachable from the optical head 29, the size of the correction tool can be less than the size of the resin plate 65 which covers the entire scanning region of the optical head 29. In addition, since the fluorescent light FL is always emitted from only one point of the resin plate 108 and is constant, it is possible to further improve the accuracy of shading correction.

Fourth Embodiment

Figure 18:
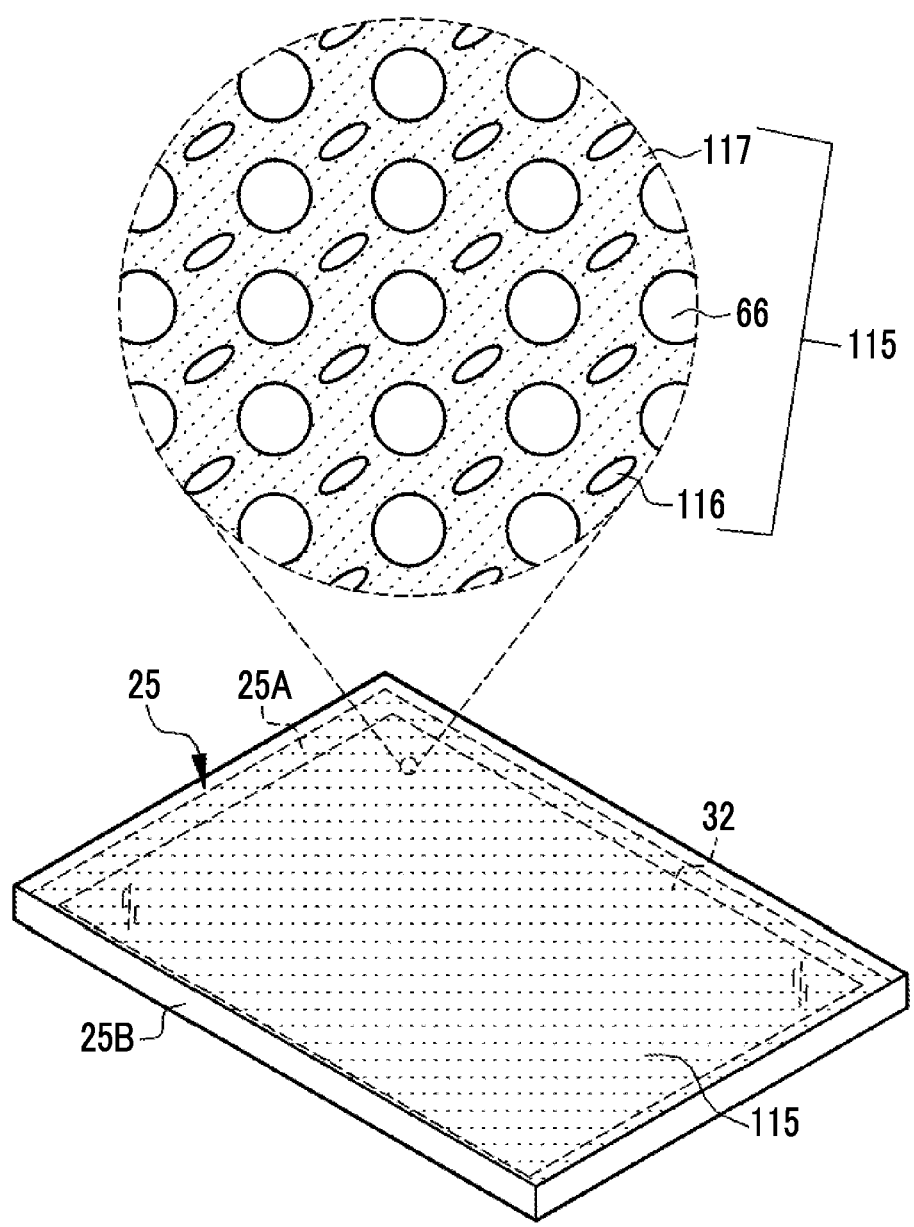
FIG. 18 is a diagram illustrating a fourth embodiment in which a correction tool is formed by a liquid in which an organic fluorescent material is mixed with a solvent and a stage filled with the liquid.

In each of the above-described embodiments, the resin plate 65 is given as an example of the correction tool. However, the invention is not limited thereto. As illustrated in FIG. 18, a correction tool may be formed by the stage 25.

In FIG. 18, the inside of the stage 25 surrounded by a side surface 25B is filled with a liquid 115. As illustrated in a circle represented by a dashed line in which a portion of the liquid 115 is enlarged and displayed, the liquid 115 is obtained by mixing an organic fluorescent material 66 and a light diffusing material 116 with a solvent 117. The light diffusing material 116 is, for example, any one of milk powder, milk, and titanium oxide powder. In addition, the solvent 117 is, for example, any one of ethanol, glycerin, and ethylene glycol, a mixed solution of at least two of ethanol, glycerin, and ethylene glycol, or an aqueous solution of any one of ethanol, glycerin, and ethylene glycol.

As such, instead of the resin plate 65, a correction tool can be formed by the liquid 115 obtained by mixing the organic fluorescent material 66 and the light diffusing material 116 with the solvent 117 and the stage 25 filled with the liquid 115. In the case of the resin plate 65, it is necessary to manufacture the resin plate 65 according to various stages 25. However, since the liquid 115 has no definite shape, it is possible to respond to the stage 25 with various sizes. Since the light diffusing material 116 is mixed, it is possible to generate uniform fluorescent light from the entire surface.

The image carrier 13 is scanned after the stage 25 is cleaned and the liquid 115 is removed from the stage 25. In this case, there is no gap between the image carrier 13 and the glass plate 32 unlike the resin plate 65 according to the first embodiment. Therefore, there is no concern that the Newton ring will be generated. As a result, the roughening process according to the first embodiment is not required.

Fifth Embodiment

Figure 19:
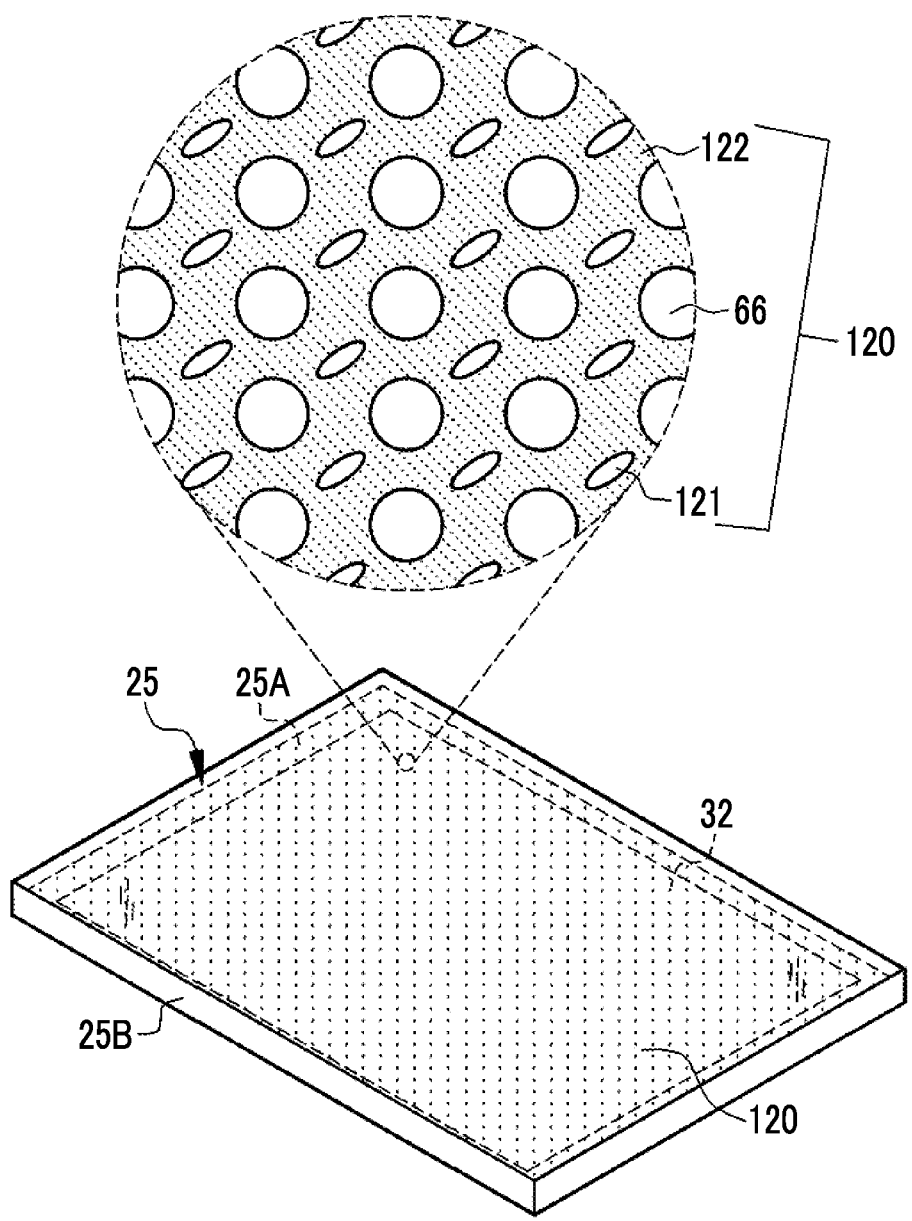
FIG. 19 is a diagram illustrating a fifth embodiment in which a correction tool is formed by gel in which an organic fluorescent material is mixed with a dispersion medium and a stage filled with the gel.

A correction tool may be formed by the stage 25 as illustrated in FIG. 19. In FIG. 19, the inside of the stage 25 surrounded by the side surface 25B is filled with gel 120, instead of the liquid 115. As illustrated in a circle represented by a dashed line in which a portion of the gel 120 is enlarged and displayed, the gel 120 is obtained by mixing the organic fluorescent material 66 and a light diffusing material 121 with a dispersion medium 122. The light diffusing material 121 is, for example, any one of milk powder, milk, and titanium oxide powder, similarly to the light diffusing material 116 according to the fourth embodiment. In addition, the dispersion medium 122 is, for example, any one of agar, agarose, and polyacrylamide.

As such, instead of the resin plate 65, a correction tool can be formed by the gel 120 obtained by mixing the organic fluorescent material 66 and the light diffusing material 121 with the dispersion medium 122 and the stage 25 filled with the gel 120. Since the light diffusing material 121 is mixed, it is possible to generate uniform fluorescent light from the entire surface. In addition, since the gel 120 has no definite shape in an undiluted state, it is possible to respond to the stage 25 with various sizes, similar to the liquid 115 according to the fourth embodiment.

In this case, the image carrier 13 is scanned after the gel 120 is removed from the stage 25 as in the fourth embodiment. Furthermore, in this case, the roughening process is not required as in the fourth embodiment.

In the case of the liquid 115 according to the fourth embodiment, there is a concern that the liquid 115 will wave due to vibration associated with the movement of, for example, the optical head 29. In the case of the gel 120, the gel 120 is less likely to wave than the liquid 115. Therefore, the accuracy of shading correction can be higher than that in the case of the liquid 115. It goes without saying that the resin plate 65 according to the first embodiment is least affected by vibration associated with the movement of, for example, the optical head 29.

A correction tool may be formed by the liquid 115 or the gel 120 and a container that accommodates the liquid 115 or the gel 120 separately from the stage 25. In this case, the container that accommodates the liquid 115 or the gel 120 may be a hollow case with a plane size that covers the entire scanning region of the optical head 29 and the case may be filled with the liquid 115 or the gel 120.

In the first embodiment, the image reading apparatus 11 in which the optical axis of the excitation light EL and the optical axis of the fluorescent light FL in the optical head 29 are aligned with each other is given as an example. However, the invention is not limited thereto. An optical head 125 that is schematically illustrated in FIG. 20 may be used.

Figure 20:
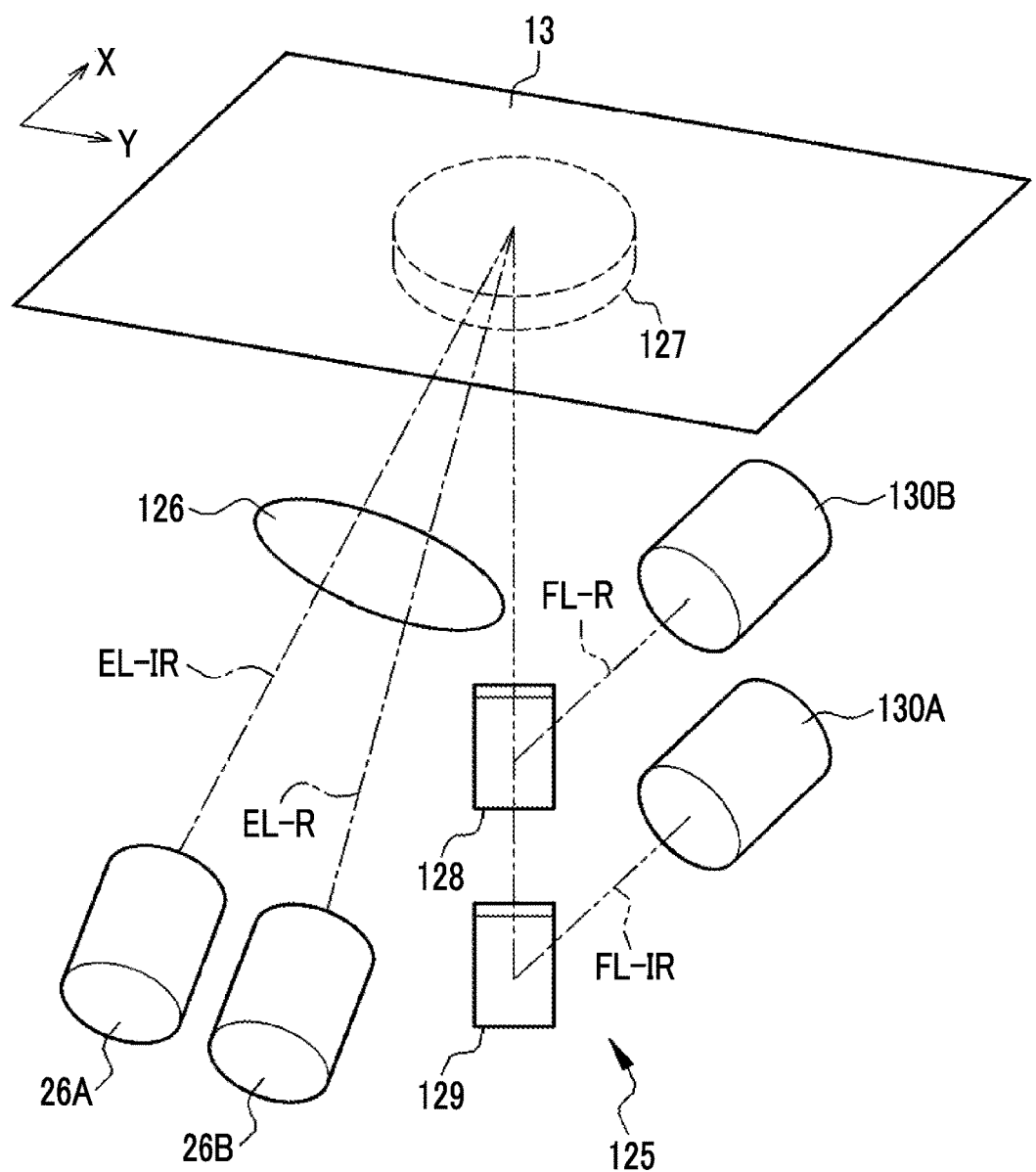
FIG. 20 is a diagram illustrating another example of the optical head.

In FIG. 20, the optical head 125 includes the infrared excitation light source 26A, the red excitation light source 26B, an objective lens 126, a condensing lens 127, a dichroic mirror 128, a mirror 129, a first avalanche photodiode (hereinafter, referred to as an APD) 130A, and a second APD 130B. These components are integrated into a module. The optical head 125 is moved in the main scanning direction X and the sub-scanning direction Y, similarly to the optical head 29 according to the first embodiment.

The objective lens 126 focuses the infrared excitation light EL-IR from the infrared excitation light source 26A and the red excitation light EL-R from the red excitation light source 26B on the image carrier 13 which is set to a stage (not illustrated). The condensing lens 127 condenses the infrared fluorescent light FL-IR and the red fluorescent light FL-R from the image carrier 13 and guides the light to the dichroic mirror 128 that is provided below the condensing lens 127.

The dichroic mirror 128 transmits the infrared fluorescent light FL-IR from the condensing lens 127 and reflects the red fluorescent light FL-R to the second APD 130B. The mirror 129 reflects the infrared fluorescent light FL-IR transmitted through the dichroic mirror 128 to the first APD 130A.

The first APD 130A and the second APD 130E photo-electrically detect the infrared fluorescent light FL-IR and the red fluorescent light FL-R at a predetermined time and output an analog image signal corresponding to the detected fluorescent light, instead of the photomultiplier 31 according to the first embodiment.

As such, the invention can also be applied to a case in which the optical head 125 in which the optical axes of the excitation light EL and the fluorescent light FL are different from each other is used. In addition, a detector for the fluorescent light FL is not limited to the photomultiplier 31 according to the first embodiment and may be the APD 130 as in the optical head 125. Furthermore, an optical head may be used in which a plurality of excitation light sources 26 and a plurality of detectors for the fluorescent light FL which correspond to the plurality of excitation light sources 26 may be optically arranged along the same axis.

A charge coupled device (CCD) area sensor may be used as the detector for the fluorescent light FL. In this case, similarly to the first embodiment, shading correction is performed using Expression (1) or Expression (2).

In each of the above-described embodiments, the example in which the acquisition unit 90 and the correction unit 96 are constructed in the CPU 77 of the console 12 and the console 12 is used as the shading correction apparatus has been described. However, the image reading apparatus 11 may have the functions of the shading correction apparatus. In this case, the acquisition unit 90 and the correction unit 96 are provided in, for example, the controller 59. In addition, a computer different from the image reading apparatus 11 and the console 12 may have the functions of the shading correction apparatus.

In each of the above-described embodiments, the correction tool includes the first correction tool and the second correction tool such as the first resin plate 65A and the second resin plate 65B. However, the correction tool may include one of the first correction tool and the second correction tool. For example, the correction tool may include only the first resin plate 65A or only the second resin plate 65B.

In the invention, the above-mentioned various embodiments or various modification examples may be appropriately combined with each other. In addition, the invention is not limited to the above-described embodiments and may have various structures without departing from the scope and spirit of the invention. Furthermore, the invention can be applied to a program and a storage medium storing the program.

EXPLANATION OF REFERENCES

10: image detection system
11: image reading apparatus
12: console (shading correction apparatus)
13: image carrier
14: housing
15, 16: cover
17: display
18: operation unit
25: stage
25A: bottom
25B: side surface
26: excitation light source
26A: excitation light source (infrared excitation light source)
26B: excitation light source (red excitation light source)
26C: excitation light source (green excitation light source)
26D: excitation light source (blue excitation light source)
27: light source optical system
28: light guide optical system
29, 125: optical head
29A: upper surface
30: filter unit
31: photomultiplier
32, 107: glass plate
33 to 36: collimator lens
37, 41, 42, 129: mirror
38, 39, 40, 128: dichroic mirror
43: perforated concave mirror
44, 50: concave mirror
45: through hole
46: substrate
47: filter
47A: filter (infrared filter)
47B: filter (red filter)
47C: filter (green filter)
47D: filter (blue filter)
47E: filter
51: aspheric lens
55: A/D converter (A/D)
56: image memory
57: communication unit
58: scanning unit
59: controller
65, 65AB-1, 65AB-2: resin plate (correction tool)
65A: first resin plate (first correction tool)
65B: second resin plate (second correction tool)
65C: third resin plate
66: organic fluorescent material
67: binder
68, 68A, 68B, 110: surface
70: Table
75: storage device
76: memory
77: CPU
78: communication unit
79: data bus
85: operation program
86: reference image
86A to 86D: first to fourth reference image
90: acquisition unit
91: command receiving unit
92: information management unit
93: image processing unit
94: setting unit
95: display control unit
96: correction unit
100: black plate
105: correction tool
106: main body
106A: inner circumferential surface
108: resin plate
109: stopper
115: liquid
116, 121: light diffusing material
117: solvent
120: gel
122: dispersion medium
126: objective lens
127: condensing lens
130A, 130B: first, second avalanche photodiode (APD)
X: main scanning direction
Y: sub-scanning direction
EL: excitation light
EL-IR: infrared excitation light
EL-R: red excitation light
FL: fluorescent light FL-IR: infrared fluorescent light
FL-R: red fluorescent light
S100 to S140, S200 to S250: step

What is claimed is:

1. A shading correction apparatus that is used in an image reading apparatus which irradiates an image carrier that carries image information and includes a fluorescent material with excitation light, detects fluorescent light emitted from the fluorescent material excited by the excitation light, and outputs a fluorescence image and corrects shading which is density unevenness in the fluorescence image, comprising:
a correction tool that includes an organic fluorescent material having wavelength characteristics in which an excitation wavelength band and an emission wavelength band at least partially overlap an excitation wavelength band and an emission wavelength band of the fluorescent material, respectively, and includes a first correction tool which includes a phthalocyanine-based pigment as the organic fluorescent material and/or a second correction tool which includes an anthraquinone-based pigment as the organic fluorescent material; and
processing circuitry configured to:
acquire a reference image which is obtained by irradiating the correction tool with the excitation light and is a reference for the shading correction; and
perform the shading correction for the fluorescence image on the basis of the reference image.

2. The shading correction apparatus according to claim 1, wherein the correction tool is used for the shading correction in a case in which the excitation light with a center wavelength greater than 650 nm is used.

3. The shading correction apparatus according to claim 2, wherein the first correction tool is used for infrared excitation light with a center wavelength of 770 nm to 800 nm, and
the second correction tool is used for red excitation light with a center wavelength of 650 nm to 690 nm.

4. The shading correction apparatus according to claim 1, wherein the correction tool is a plate obtained by dispersing the organic fluorescent material in a binder and solidifying the binder.

5. The shading correction apparatus according to claim 4, wherein, in a case in which the correction tool includes the first correction tool and the second correction tool, the first correction tool and the second correction tool are integrated with each other.

6. The shading correction apparatus according to claim 5, wherein a black plate is interposed between the first correction tool and the second correction tool.

7. The shading correction apparatus according to claim 5, wherein the first correction tool and the second correction tool are directly bonded to each other.

8. The shading correction apparatus according to claim 4, wherein the image reading apparatus includes a stage that holds the image carrier and an optical head that emits the excitation light, acquires the fluorescent light, and is moved relative to the stage, and
the correction tool has a size that covers an entire scanning region of the optical head and is held by the stage.

9. The shading correction apparatus according to claim 4, wherein the image reading apparatus includes a stage that holds the image carrier and an optical head that emits the excitation light, acquires the fluorescent light, and is moved relative to the stage, and
the correction tool is a cap type that is detachable from the optical head.

10. The shading correction apparatus according to claim 4, wherein a roughening process is performed for a surface of the correction tool.

11. The shading correction apparatus according to claim 10, wherein the roughening process is performed using any one of a solvent, fine particle powder, and a pressure die.

12. The shading correction apparatus according to claim 4, wherein the binder is any one of a vinyl chloride resin, a polycarbonate resin, a methacrylic resin, a silicone resin, and a polyacrylamide resin.

13. The shading correction apparatus according to claim 1, wherein the image reading apparatus includes a stage that holds the image carrier, and
a liquid obtained by mixing the organic fluorescent material with a solvent is poured in the stage and the correction tool is formed by the stage and the liquid.

14. The shading correction apparatus according to claim 13, wherein the solvent is mixed with a light diffusing material in addition to the organic fluorescent material.

15. The shading correction apparatus according to claim 13, wherein the solvent is any one of ethanol, glycerin, and ethylene glycol, a mixed solution of at least two of ethanol, glycerin, and ethylene glycol, or an aqueous solution of any one of ethanol, glycerin, and ethylene glycol.

16. The shading correction apparatus according to claim 1, wherein the image reading apparatus includes a stage that holds the image carrier, and
gel obtained by mixing the organic fluorescent material with a dispersion medium is poured in the stage and the correction tool is formed by the stage and the gel.

17. The shading correction apparatus according to claim 16, wherein the dispersion medium is mixed with a light diffusing material in addition to the organic fluorescent material.

18. The shading correction apparatus according to claim 16, wherein the dispersion medium is any one of agar, agarose, and polyacrylamide.

19. A method for operating a shading correction apparatus that is used in an image reading apparatus which irradiates an image carrier that carries image information and includes a fluorescent material with excitation light, detects fluorescent light emitted from the fluorescent material excited by the excitation light, and outputs a fluorescence image and corrects shading which is density unevenness in the fluorescence image, the method comprising:
acquiring a reference image which is a reference for the shading correction and is obtained by irradiating, with the excitation light, a correction tool that includes an organic fluorescent material having wavelength characteristics in which an excitation wavelength band and an emission wavelength band at least partially overlap an excitation wavelength band and an emission wavelength band of the fluorescent material, respectively, and includes a first correction tool which includes a phthalocyanine-based pigment as the organic fluorescent material and/or a second correction tool which includes an anthraquinone-based pigment as the organic fluorescent material; and performing the shading correction for the fluorescence image on the basis of the reference image.

* * * * *